US006228371B1

(12) United States Patent
Nano

(10) Patent No.: US 6,228,371 B1
(45) Date of Patent: May 8, 2001

(54) *MYCOBACTERIUM TUBERCULOSIS* DNA SEQUENCES ENCODING IMMUNOSTIMULATORY PEPTIDES

(75) Inventor: Francis E. Nano, Victoria (CA)

(73) Assignee: University of Victoria Innovation and Development Corp., Victoria (CA)

( * ) Notice: Subject to any disclaimer, the term of this patent is extended or adjusted under 35 U.S.C. 154(b) by 0 days.

(21) Appl. No.: 08/990,823

(22) Filed: Dec. 15, 1997

Related U.S. Application Data

(63) Continuation-in-part of application No. PCT/US96/10375, filed on Jun. 14, 1996

(60) Provisional application No. 60/000,254, filed on Jun. 15, 1995.

(51) Int. Cl.[7] .......................... C12Q 1/68; A61K 39/04; C12N 1/21; C07H 21/04

(52) U.S. Cl. ....................... 424/248.1; 435/6; 435/252.3; 435/320.1; 530/350; 536/23.7; 536/24.32

(58) Field of Search ............................ 424/184.1, 185.1, 424/190.1, 234.1, 248.1; 435/6, 252.3, 252.33, 320.1; 530/300, 324, 325, 326, 327, 328, 329, 330, 387.1; 536/23.1, 23.7, 24.32, 24.33

(56) References Cited

U.S. PATENT DOCUMENTS

| | | | |
|---|---|---|---|
| 5,168,039 | * 12/1992 | Crawford et al. | 435/6 |
| 5,573,915 | * 11/1996 | Barry, III et al. | 435/6 |

OTHER PUBLICATIONS

Young et al. (1985) Dissection of Mycobacterium tuberculosis antigens using recombinant DNA. Proc. Natl. Acad. Sci. USA 82:2583–2587, May 1985.*

Skamene, E. (1989). Genetic control of susceptibility of Mycobacterial infections. *Ref. Infect. Dis.* 11:S394–S399.

Kaufmann, S.H.E. (1991). Role of T–Cell Subsets in Bacterial Infections. *Current Opinion in Immunology* 3:465–470.

Orme, I.M., et al. (1992). T Lymphocytes Mediating Protection and Cellular Cytolysis During the Course of Mycobacterium–Tuberculosis Infection—Evidence for Different Kinetics and Recognition of a Wide Spectrum of Protein Antigens. *Journal of Immunology* 148:189–196.

Daugelat, S., et al. (1992). Secreted Antigens of Mycobacterium tuberculosis: characterization with T Lymphocytes from Patients and Contacts after Two–Dimensional Separation. *J. Infect. Dis.* 166:186–190.

Barnes et al. (1989). Characterization of T–Cell Antigens Associated with the Cell Wall Protein–Peptidoglycan Complex of *Mycobacterium tuberculosis. J. Immunol.* 143:2656–2662.

Collins et al. (1988). Biological activity of protein antigens isolated from *Mycobacterium tuberculosis* culture filtrate. *Infect. Immun.* 56:1260–1266.

Lamb et al. (1989). Identification of Mycobacterial Antigens Recognized by T Lymphocytes. *Rev. Infect. Dis.* 11:S443–S447.

Pal P.G., et al. (1992). Immunization with Extracellular Proteins of Mycobacterium tuberculosis Induces Cell–Mediated Immune Responses and Substantial Protective Immunity in a Guinea Pig Model of Pulmonary Tuberculosis. *Infect. Immun.* 60:4781–4792.

Andersen (1994). Effective Vaccination of Mice against *Mycobacterium tuberculosis* Infection with a Soluble Mixture of Secreted Mycobacterial Proteins. *Infection & Immunity* 62:2536–2544.

Jardim et al. (1990). Immunoprotective *Leishmania major* Synthetic T Cell Epitopes. *J. Exp. Med.* 172:645–648.

Orme et al. (1993). Cytokine Secretion by CD4 T Lymphocytes Acquired in Response to *Mycobacterium tuberculosis* Infection. *J. Immunology* 151:518–525.

Boesen et al. (1995). Human T–Cell Responses to Secreted Antigen Fractions of *Mycobacterium tuberculosis. Infection and Immunity* 63:1491–1497.

Mougneau et al. (1995). Expression Cloning of a Protective *Leishmania* Antigen. *Science* 268:536–566.

Mdluli et al. (1995). New vectors for the in vitro generation of alkaline phosphatase fusions to proteins encoded by G+C–rich DNA. *Gene* 155:133–134.

Tommassen et al. (1993). Use of the enterobacterial outer membrane protein PhoE in the development of new vaccines and DNA probes. *Intl. J. Microbiol. Virol. Parasitol. infect. Dis.* 278: 396–406.

Janssen et al. (1994). Immunogenicity of a mycobacterial T–cell epitope expressed in outer membrane protein PhoE of *Escherichia coli. Vaccine* 12: 406–409.

Lim et al. (1995). Identification of Mycobacterium tuberculosis DNA sequences encoding exported proteins by using phoA gene fusions. *J. Bacteriol.* 177: 59–65.

Oettinger et al. (1994). Cloning and B–Cell Epitope Mapping of MPT64 from *Mycobacterium tuberculosis* H37Rv. *Infection and Immunity* 62: 2058–2064.

Young et al. (1988). Stress proteins are immune targets in leprosy and tuberculosis. *Proc. Natl. Acad. Sci. USA* 85: 4267–4270.

* cited by examiner

*Primary Examiner*—Robert A. Schwartzman
(74) *Attorney, Agent, or Firm*—Klarquist Sparkman Campbell Leigh & Whinston LLP

(57) ABSTRACT

Nucleotide sequences isolated from *Mycobacterium tuberculosis* are disclosed. These sequences are shown to encode immunostimulatory peptides. The invention encompasses, among other things, vaccine preparations formulated using these peptides.

23 Claims, 4 Drawing Sheets

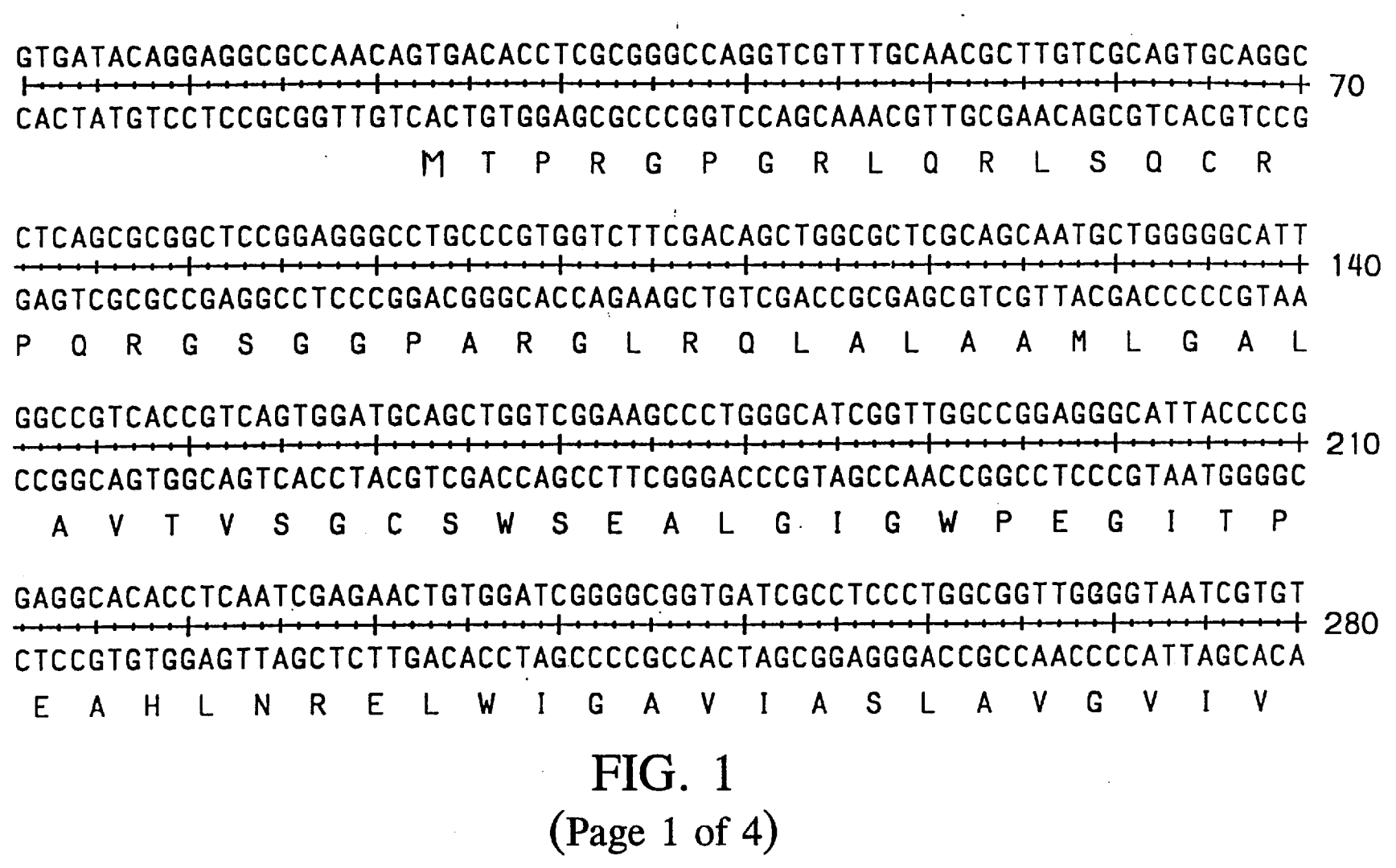

```
GTGATACAGGAGGCGCCAACAGTGACACCTCGCGGGCCAGGTCGTTTGCAACGCTTGTCGCAGTGCAGGC
                                                                       70
CACTATGTCCTCCGCGGTTGTCACTGTGGAGCGCCCGGTCCAGCAAACGTTGCGAACAGCGTCACGTCCG
                     M  T  P  R  G  P  G  R  L  Q  R  L  S  Q  C  R

CTCAGCGCGGCTCCGGAGGGCCTGCCCGTGGTCTTCGACAGCTGGCGCTCGCAGCAATGCTGGGGGCATT
                                                                       140
GAGTCGCGCCGAGGCCTCCCGGACGGGCACCAGAAGCTGTCGACCGCGAGCGTCGTTACGACCCCCGTAA
P  Q  R  G  S  G  G  P  A  R  G  L  R  Q  L  A  L  A  A  M  L  G  A  L

GGCCGTCACCGTCAGTGGATGCAGCTGGTCGGAAGCCCTGGGCATCGGTTGGCCGGAGGGCATTACCCCG
                                                                       210
CCGGCAGTGGCAGTCACCTACGTCGACCAGCCTTCGGGACCCGTAGCCAACCGGCCTCCCGTAATGGGGC
  A  V  T  V  S  G  C  S  W  S  E  A  L  G  I  G  W  P  E  G  I  T  P

GAGGCACACCTCAATCGAGAACTGTGGATCGGGGCGGTGATCGCCTCCCTGGCGGTTGGGGTAATCGTGT
                                                                       280
CTCCGTGTGGAGTTAGCTCTTGACACCTAGCCCCGCCACTAGCGGAGGGACCGCCAACCCCATTAGCACA
 E  A  H  L  N  R  E  L  W  I  G  A  V  I  A  S  L  A  V  G  V  I  V
```

FIG. 1
(Page 1 of 4)

```
GGGGTCTCATCTTCTGGTCCGCGGTATTTCACCGGAAGAAGAACACCGACACTGAGTTGCCCCGCCAGTT
---------+---------+---------+---------+---------+---------+---------+ 350
CCCCAGAGTAGAAGACCAGGCGCCATAAAGTGGCCTTCTTCTTGTGGCTGTGACTCAACGGGGCGGTCAA
W  G  L  I  F  W  S  A  V  F  H  R  K  K  N  T  D  T  E  L  P  R  Q  F

CGGCTACAACATGCCGCTAGAGCTGGTTCTCACCGTCATACCGTTCCTCATCATCTCGGTGCTGTTTTAT
---------+---------+---------+---------+---------+---------+---------+ 420
GCCGATGTTGTACGGCGATCTCGACCAAGAGTGGCAGTATGGCAAGGAGTAGTAGAGCCACGACAAAATA
  G  Y  N  M  P  L  E  L  V  L  T  V  I  P  F  L  I  I  S  V  L  F  Y

TTCACCGTCGTGGTGCAGGAGAAGATGCTGCAGATAGCCAAGGATCCCGAGGTCGTGATTGATATCACGT
---------+---------+---------+---------+---------+---------+---------+ 490
AAGTGGCAGCACCACGTCCTCTTCTACGACGTCTATCGGTTCCTAGGGCTCCAGCACTAACTATAGTGCA
 F  T  V  V  V  Q  E  K  M  L  Q  I  A  K  D  P  E  V  V  I  D  I  T

CTTTCCAGTGGAATTGGAAGTTTGGCTATCAAAGGGTGAACTTCAAAGACGGCACACTGACCTATGATGG
---------+---------+---------+---------+---------+---------+---------+ 560
GAAAGGTCACCTTAACCTTCAAACCGATAGTTTCCCACTTGAAGTTTCTGCCGTGTGACTGGATACTACC
S  F  Q  W  N  W  K  F  G  Y  Q  R  V  N  F  K  D  G  T  L  T  Y  D  G
```

FIG. 1
(Page 2 of 4)

```
TGCCGATCCGGAGCGCAAGCGCGCCATGGTTTCCAAGCCAGAGGGCAAGGACAAGTACGGCGAAGAGCTG 630
ACGGCTAGGCCTCGCGTTCGCGCGGTACCAAAGGTTCGGTCTCCCGTTCCTGTTCATGCCGCTTCTCGAC
  A  D  P  E  R  K  R  A  M  V  S  K  P  E  G  K  D  K  Y  G  E  E  L

GTCGGGCCGGTGCGCGGGCTCAACACCGAGGACCGGACCTACCTGAATTTCGACAAGGTCGAGACGTTGG 700
CAGCCCGGCCACGCGCCCGAGTTGTGGCTCCTGGCCTGGATGGACTTAAAGCTGTTCCAGCTCTGCAACC
 V  G  P  V  R  G  L  N  T  E  D  R  T  Y  L  N  F  D  K  V  E  T  L

GCACCAGCACCGAAATTCCGGTGCTGGTGCTGCCGTCCGGCAAGCGTATCGAATTCCAAATGGCCTCAGC 770
CGTGGTCGTGGCTTTAAGGCCACGACCACGACGGCAGGCCGTTCGCATAGCTTAAGGTTTACCGGAGTCG
G  T  S  T  E  I  P  V  L  V  L  P  S  G  K  R  I  E  F  Q  M  A  S  A

CGATGTGATACACGCATTCTGGGTGCCGGAGTTCTTGTTCAAGCGTGACGTGATGCCTAACCCGGTGGCA 840
GCTACACTATGTGCGTAAGACCCACGGCCTCAAGAACAAGTTCGCACTGCACTACGGATTGGGCCACCGT
  D  V  I  H  A  F  W  V  P  E  F  L  F  K  R  D  V  M  P  N  P  V  A
```

FIG. 1
(Page 3 of 4)

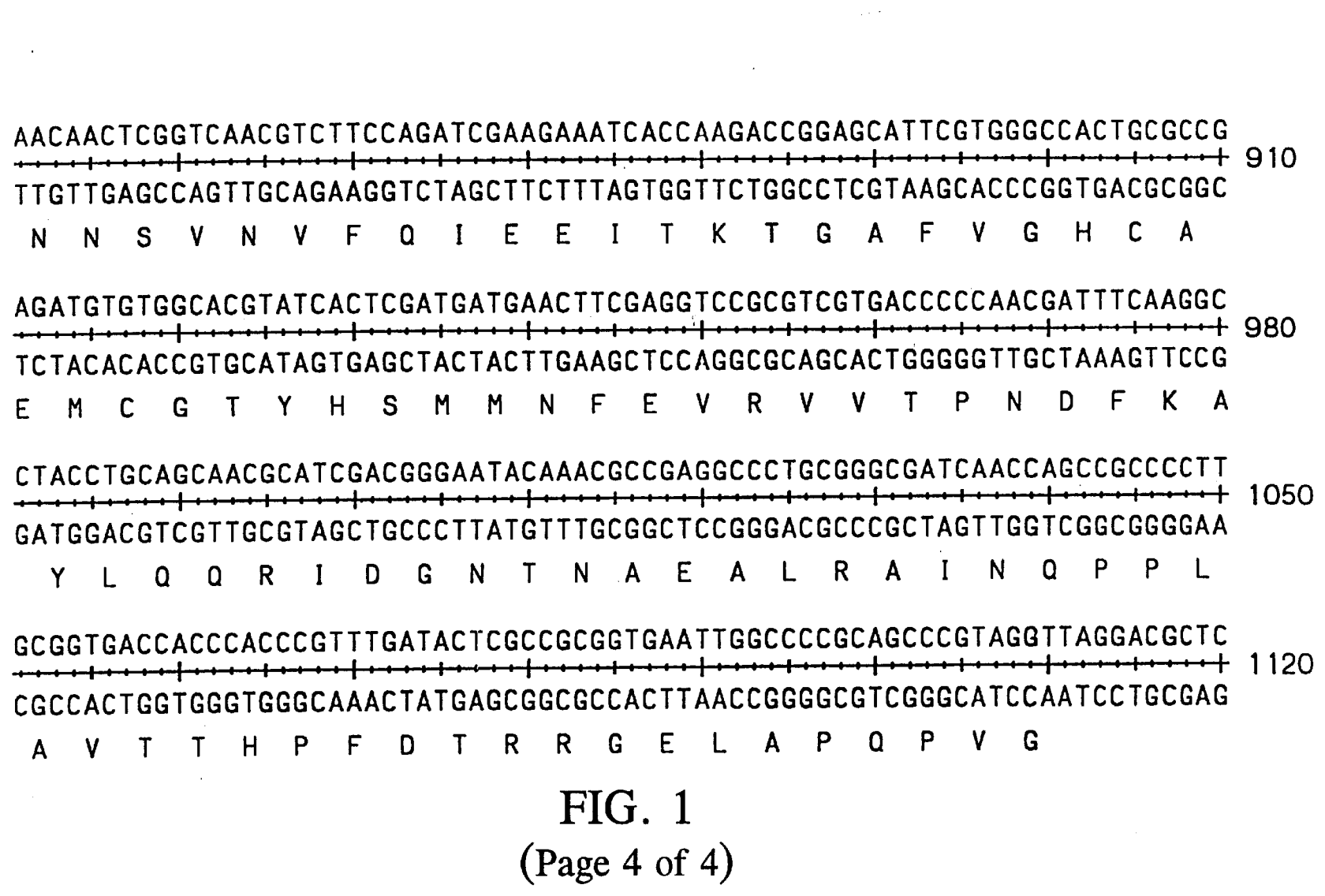

```
AACAACTCGGTCAACGTCTTCCAGATCGAAGAAATCACCAAGACCGGAGCATTCGTGGGCCACTGCGCCG 910
TTGTTGAGCCAGTTGCAGAAGGTCTAGCTTCTTTAGTGGTTCTGGCCTCGTAAGCACCCGGTGACGCGGC
 N  N  S  V  N  V  F  Q  I  E  E  I  T  K  T  G  A  F  V  G  H  C  A

AGATGTGTGGCACGTATCACTCGATGATGAACTTCGAGGTCCGCGTCGTGACCCCCAACGATTTCAAGGC 980
TCTACACACCGTGCATAGTGAGCTACTACTTGAAGCTCCAGGCGCAGCACTGGGGGTTGCTAAAGTTCCG
E  M  C  G  T  Y  H  S  M  M  N  F  E  V  R  V  V  T  P  N  D  F  K  A

CTACCTGCAGCAACGCATCGACGGGAATACAAACGCCGAGGCCCTGCGGGCGATCAACCAGCCGCCCCTT 1050
GATGGACGTCGTTGCGTAGCTGCCCTTATGTTTGCGGCTCCGGGACGCCCGCTAGTTGGTCGGCGGGGAA
  Y  L  Q  Q  R  I  D  G  N  T  N  A  E  A  L  R  A  I  N  Q  P  P  L

GCGGTGACCACCCACCCGTTTGATACTCGCCGCGGTGAATTGGCCCCGCAGCCCGTAGGTTAGGACGCTC 1120
CGCCACTGGTGGGTGGGCAAACTATGAGCGGCGCCACTTAACCGGGGCGTCGGGCATCCAATCCTGCGAG
 A  V  T  T  H  P  F  D  T  R  R  G  E  L  A  P  Q  P  V  G
```

FIG. 1
(Page 4 of 4)

SEQUENCE LISTING

```
<160> NUMBER OF SEQ ID NOS: 113

<210> SEQ ID NO: 1
<211> LENGTH: 267
<212> TYPE: DNA
<213> ORGANISM: Mycobacterium tuberculosis

<400> SEQUENCE: 1

acgcggacct cgaagttcat catcgagtga tacgtgccac acatctcggc gcagtggccc     60

acgaatgctc cggtcttggt gatttcttcg atctggaaga cgttgaccga gttgtttgcc    120

accgggttag gcatcacgtc acgcttgaac aagaactccg gcacccagaa tgcgtgtatc    180

acatcggctg aggccatttg gaattcgata cgcttgccgg acggcagcac cagcaccgga    240

atttcggtgc tggtgcccaa cgtctcg                                        267


<210> SEQ ID NO: 2
<211> LENGTH: 487
<212> TYPE: DNA
<213> ORGANISM: Mycobacterium tuberculosis
<220> FEATURE:
<221> NAME/KEY: Modified base
<223> OTHER INFORMATION: n represents a or g or c or t/u
```

-continued

<400> SEQUENCE: 2

```
ctgatacgac gccggcaagg actacgacga ggtggcacag aattcaatgc ggcgctcatc     60
ggaaccgacg tgcccgacgt cgttttgctc gacgacngat ggtggttcca tttcgccntc    120
agcggtgttc tgactgccct tgacgacctg ttcggccaag ttggggtgga cacaacggat    180
tacgtcgatt cgctgctggc cgactatgag ttcaacggcc gccattacgc tgtgccgtat    240
gctcgctcga cgccgctgtt ctactacaac aaggcggcgt ggcaacaggc cggcctaccc    300
gaccgcggac cgcaatcctg gtcagagttc gacgagtggg gtccggagtt acagcgcgtg    360
gtcggcgccg gtcgatcggc gcacggctgc gntaacgccg acctcatctc gtggacgttt    420
cagggaccga actgggcatt cggcggtgcc tactccgaca agtggacatt gacattgacc    480
gagcccg                                                              487
```

<210> SEQ ID NO: 3
<211> LENGTH: 511
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 3

```
ggcggccaga cngtcnggaa ctcgcnggcc attggtgtgg tgggaaccgc gatcctcgac     60
gcaccgcttc gcggtcttgc agtgttcgat gccaatctgc cggccgggac gctgccggat    120
ggcggcccgt tcaccgaggc tggtgacaag acctggcgtg tcgttccggg cactactccc    180
caggtcggtc aaggcaccgt caaagtgttc aggtataccg tcgagatcga gaacggtctt    240
gatcccacaa tgtacggcgg tgacaacgca ttcgcccaga tggtcgacca gacgttgacc    300
aatcccaagg gctggaccca caatccgcaa ttcgcgttcg tgcggatcga cagcggaaaa    360
cccgacttcc ggatttcgct ggtgtcgccg acgacagtgc gcggggggtg tggctacgaa    420
ttccggctcg agacgtcctg ctacaacccg tcgttcggcg gcatggatcg ccaatcgcgg    480
gtgttcatca acgaggcgcg ctgggtacgc g                                   511
```

<210> SEQ ID NO: 4
<211> LENGTH: 512
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 4

```
gtgtgcaacc agtgtgtgtn cgtgtgcgaa ccagtgtgta gtggtaacca ggaccacgtt     60
gcaaaccagt gttggagtgc agtgttgcgt gcnagtgttg cncgttgcag tgttngncga    120
gccgagattg gaagttnccg acattaccgt tgccgacgtt gccctcgccg acgttcgcca    180
agcccaggtt gcggacacgc cggtgattgt gcgtggggca atgancgggc tgctggcccg    240
gccgaattcc aaggcgtcga tcggcacggt gttccaggac cgggccgctc gctacggtga    300
ccgagtcttc ctgaaattcg gcgatcagca gctgacctac cgcgacgcta acgccaccgc    360
caaccggtac gccgcggtgt tggccgcccg cggcgtcggc cccggcgacg tcgttggcat    420
catgttgcgt aactcaccca gcacagtctt ggcgatgctg gccacggtca agtgcggcgc    480
tatcgccggc atgctcaact accaccagcg cg                                  512
```

-continued

<210> SEQ ID NO: 5
<211> LENGTH: 456
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 5
gcaacggaga ggtggactat gccggaccgg caccgcgaag gggttggtgc cggcccgggt 60
ggtgacggtg cacattctgc gcaattcgct gagttccggt ggtgaccttc ctgggcgcgg 120
agtctgggcg cgctgatggc ggagcgaktg tgaccgaagg aantcngttc aacatccacg 180
gcgtcggggg cgtgctgtat caagcggtca ccgtcaggag acgccgacgg tggtgtcgat 240
cgtgacggtg ctggtgctga tctacctgat caccaatctg ttggtggatc tgctgtatgc 300
ggccctggac gccgnngatn cgctatggct gagcacacgg ggttctggct cgatgcctng 360
cgcgggttgc gccggcgtcc taaantcgtg atcgcgcggc gctgakcctg ctgattcttg 420
tcgtggcggc gtttccgtcg ttgtttaccg cagccg 456

<210> SEQ ID NO: 6
<211> LENGTH: 172
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 6
tcncttatcg cttcagctgg catctgccca aggaccgaat ctggacctat gacggccagc 60
tgaagatggc ccgcgacgaa gggcgttggc acgttcgctg gaccaccagc gggttgcatc 120
ccaagctagg cgaacatcaa aggttcgcgc tacgagccga cccgccgcgg cg 172

<210> SEQ ID NO: 7
<211> LENGTH: 232
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 7
cttctcgcgc cagcncgtcc cgctgtccgg gatgncgcta ccggtcgtca gcgccaagac 60
ggtgcagctc aacgacggcg ggttggtgcg cacggtgcac ttgccggccc ccaatgtcgc 120
ggggctgctg agtgcggccn gcgtgccgct gttgcaaagc gaccacgtgg tgcccgccgc 180
gacggccccg atcgtcgaag gcatgcagat ccaggtgacc cgcaaatcgg at 232

<210> SEQ ID NO: 8
<211> LENGTH: 173
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 8
gttcgncgcg ctcaaaaggt tgacgatggt cacgtcgcac gtgctggccg agaccaaggt 60
ggatttcggt gaagacctca aaganctcta ctcgnatcgt caaggccctc aacgacgacc 120
gaaaggattt cgtcacctcg ctgcagctgt tgctgacgtt cccatttccc aac 173

-continued

<210> SEQ ID NO: 9
<211> LENGTH: 223
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 9
cctgttncaa cggtncnttc ncggaacgga cgacttctga tncgnnctcg gncgttccct 60
cgcaccggtc gatggtgatc aaggtcagcg tcttcgcggt ggtcatgctg ctggtggccg 120
ccggtctggt ggtggtattc ggggacttcc ggtttggtcc cacaaccgtc taccacgcca 180
ccttcaccga cncgtngcgg ctgaangcag gccagaaggt tcg 223

<210> SEQ ID NO: 10
<211> LENGTH: 120
<212> TYPE: DNA
<213> ORGANISM: Mycobacterium tuberculosis

<400> SEQUENCE: 10
caacgagatc gcacccgtga ttaggaggtg acggtggcag cgccgacccc gtcgaatcgg 60
atcgaagtaa cgctccgtag acgccagctc gtccgcgccg atgccgacct gccacccgtg 120

<210> SEQ ID NO: 11
<211> LENGTH: 162
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 11
cggcttccag cgggtgcgcc aagcacggcc ggtccgtgcg agatcgtccc caatggcacg 60
ccggcgccca agacaccccc ggntaccgtg ccttcgtcgc gcaacctcgc gaccaacccc 120
gagatcgcca ccnnctacng ccgggacatg accgtggtgc gg 162

<210> SEQ ID NO: 12
<211> LENGTH: 133
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 12
gactggnccc gaygytgtgn ccgghncgth ggncghgchg cantcgaycc tggccgttgc 60
ttcggtgccg ggttgttcat cgccttcgac cagttgtggc gctggaacag catagtggcg 120
ctagtgctat cgg 133

<210> SEQ ID NO: 13
<211> LENGTH: 395
<212> TYPE: DNA
<213> ORGANISM: Mycobacterium tuberculosis

<400> SEQUENCE: 13
gcgcacactg cgcatgctgc cgtacccgcg ccaggcatga gtcttaggcc gaaatgcctg 60
gttaactggc gtgtcgtggt tgacccgcgg gcgtgcggct acagtgcatg ctgtgatcgg 120
cagtgggaga ggtagcggtg cggcgtaagg tgcggaggtt gactctggcg gtgtcggcgt 180

-continued

```
tggtggcttt gttcccggcg gtcgcggggt gctccgattc cggcgacaac aaaccgggag    240

cgacgatccc gtcgacaccg gcaaacgctg agggccggca cggacccttc ttcccgcaat    300

gtggcggcgt cagcgatcag acggtgaccg agctgacaag ggtgaccggg ctggtcaaca    360

ccgccaagaa gtcggtgggc tgccaatggc tggcg                               395
```

<210> SEQ ID NO: 14
<211> LENGTH: 175
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 14

```
ccagnccncc naacntgtyn cgntctcayy tcgccgtcgc tgccggtncg tgtgtgcacc     60

atctgcaccg acccgtgkaa cytcgatcac ganactggna gagntcaggc atnaaagccg    120

gagtggcaca gcaacggtcg ctactggaat tggcgaagct ggatgctgag ctgac         175
```

<210> SEQ ID NO: 15
<211> LENGTH: 265
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 15

```
gggctggatt cgaggctcng tgcatgccgt acgactaggg gtagcgccca gctgctcaat     60

accatcggtt ggataacaaa ggctgaacat gaatggcttg atctcacaag cgtgcggctc    120

ccaccgaccc cggcgcccct cgagcctggg ggctgtcgcg atcctgatcg cggcgacact    180

tttcgcgact gtcgttgcgg ggtgcgggaa aaaaccgacc acggcgagct ccccgagtcc    240

cgggtcgccg tcgccggaag cccac                                          265
```

<210> SEQ ID NO: 16
<211> LENGTH: 170
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 16

```
cgccatgncg aagcgmaccc cggtccggaa ggcctgcaca gttctagccg tgctcgccgc     60

gacgctactc ctcgcctgcg gcggtcccac gcagccacgc agcatcacct tgacctttat    120

ncgcaacgcg caatcccagg ccaacgccga cgggatcatc gacaccgaca               170
```

<210> SEQ ID NO: 17
<211> LENGTH: 181
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 17

```
accngttccc gccggnctna cncncggtgc cgttgcaccg gccanctgca gcctgccccg     60

acgccgaagt ggtgttcgcn ccgcggccgc ttcgaaccgc ccgggattgg cacggtcggc    120

aabgcattcg tcagcnntgc gctcgaaggt caacaagaat gtcggggtct acgcggtgaa    180
```

-continued

```
a                                                                    181

<210> SEQ ID NO: 18
<211> LENGTH: 95
<212> TYPE: DNA
<213> ORGANISM: Mycobacterium tuberculosis

<400> SEQUENCE: 18

aggtkacggt ggcagcgccg accccgtcga atcggwtcga agaaygctcc gkacacgcca     60

gctgcgtccg ygccgatgcc gacctgccac ccgtg                                95

<210> SEQ ID NO: 19
<211> LENGTH: 283
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 19

gcgcatgcgc aaccacttgg aatccgttga caatcgcatc ggtggccggc ccgtcggtga     60

ccgcntgcaa cagcgcggtg gtcaccnaca gcgaaaccag gtncttgtcg gctccggagg    120

tggcgatgac gtggcgccgg gaggtgttga gggtcatgtc gttttcgcgn taggtgccct    180

cgatgattga tgacggaaag cnncgtngaa anttggcnat agcggcgttt gtggtctgcn    240

atncgagcra ttnctgnctg tcagtgtagn cgtgtgtgat ggc                      283

<210> SEQ ID NO: 20
<211> LENGTH: 156
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 20

tcttctacaa ggacgccttc gccaagcacc aggagctgtt cgacgacttg gncgtcaacg     60

tcaacaatgg cttgtccgat ctgtacragc aagwtcgagt cgctgccgnb cgcaacgcga    120

cgagatcatc gaggacctac accgttgcca cgaaca                               156

<210> SEQ ID NO: 21
<211> LENGTH: 123
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 21

atnccgttcc actnccgcgg cagcagctgg ntttgcgcac acggtgaccc agtggcgntt     60

ggtggggcct cgctgacggc gagtntggnc gagcgtcctc ggtcggtgnc ctntcntccc    120

gcc                                                                  123

<210> SEQ ID NO: 22
<211> LENGTH: 823
<212> TYPE: DNA
<213> ORGANISM: Mycobacterium tuberculosis
<220> FEATURE:
<221> NAME/KEY: Modified base
<223> OTHER INFORMATION: n represents a or g or c or t/u
```

-continued

<400> SEQUENCE: 22
cggtcacgca attgatggcc gcgcgcaagg scgcatggtg gagatgncca accacaccac 60
cggctgggtc cgcatggact tcgtggttcc cagtcgcggc ctgattgggt ggcgcaccga 120
cttcctcacc gagacccgtg gctccggtgt cgggcatgcg gtgttcgacg gatnaccggc 180
catgggcggg ggagkccggg cccgnccaca ccggttctct ggtatcggac cgggccggcg 240
ccatcacacc gttcgcgttg ctgcaactcg ccgatcgggg gcagttcttc gtcgagcccg 300
gccaacagan ccntacgagg ncantggctg ctgggatcaa cccccgtccg gaggacctcg 360
acatcaatgt cacccggagn agnangctga ccnaacatgc gctcatcgac cgcggatgtc 420
atcgagacgg tngccaagcc gctgcagctg gatctcgagc gcgccatgga gttatgtgcg 480
cccgacgaat gcgtcgaggt gaccccggag atcgtgcgga tccgcaaagt cgagctggcc 540
gccgccgccc gggctcgcag ccgggcgcgc accaaggcgc gtggctagca acttggcgcg 600
ctggccgcgc gagcgtaacg ccactgcgaa atccagcccg gcttttcgca gccgggttac 660
gctcgtgggg gtactggata gcctgatggg cgtgcccagc ccagtccgcc gcgtctgtgt 720
gacggtcggc gcgttggtcg cgctggcgtg tatggtgttg gccgggtgca cggtcagccc 780
gccgccggca ccccagagca ctgatacgcc gcgcagcaca ccg 823

<210> SEQ ID NO: 23
<211> LENGTH: 103
<212> TYPE: DNA
<213> ORGANISM: Mycobacterium tuberculosis

<400> SEQUENCE: 23
cttccggcgg gacaacaaca ggtctcaccg gcgccacacc ctgacacctg atcgcgtctg 60
ccgatcccgg tcggagcacc cgggttccac cgctgtgccc ccc 103

<210> SEQ ID NO: 24
<211> LENGTH: 207
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 24
gccaccggtt catcgcgtgg tgctggtcac cgccnggaan gcctcagcgg atcccctgct 60
gccaccgccg cctatccctg ccccagtctc ggcgccggca acagtcccgy ccgtgcagaa 120
cctcacggct ncthccgggc gggagcagca acaggttctc accggygccw ngyacccgca 180
ccgatcgcgt cgccgattcc ggtcgga 207

<210> SEQ ID NO: 25
<211> LENGTH: 204
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 25
ttncgcannc gttcatccag gtccactggt gtcgcanctc tcnntgatgc accggttccg 60
gatatatgtc nacatcnccs tcstcgtcct ggtgctggta ctnacgaacc tgatcgcgca 120
tttcaccaca ccgtgngcga gcatcgccac cgtcccggcc gccygcggtc ggactggtga 180
tcttggtkcg gagtagaggc ctgg 204

-continued

<210> SEQ ID NO: 26
<211> LENGTH: 207
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 26
ataccngtca tccngcacat ngtcaacctn gagtcggtnc tcacctacga ggcacgcccg 60
agatgcatca ctggtgctcg rtcagncctt cacggcttgg ccgccttccg gtaggaccgt 120
hgcatgcccg tcttcggcgc ctcgggtgtt cggtcctggc tctcgggctg ctggccnctg 180
cgccccaccc cgcaccgggc cggcttc 207

<210> SEQ ID NO: 27
<211> LENGTH: 289
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 27
ccgtgatngg ccggnncgnc atgttacggg nagccgggna ttgcgntacg ccacggtgat 60
cgcgctggtg gccgcgctgg tggncngcgt gtacgtgctc tcgtccaccg gtaataagcg 120
caccatcgtg ggctacttca cctctgctgt cgggctctat cccggtgacc aggtccgcgt 180
cctgggcgtc ccggtgggtg agatcgacat gatcgagccg cggtcgtccg acgtcaagat 240
cactatgtcg gtgtccaagg acgtcaaggt gcccgtgsac gtgcaggcc 289

<210> SEQ ID NO: 28
<211> LENGTH: 198
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 28
ttgnaccang cctatcgcaa gccaatcacc tatgacacgc tgtggcaggc tgacaccgat 60
ccgctgccag tcgtcttccc cattgtgcaa ggtgaactga gcaangcaga ccggacaaca 120
ggtatcgata gcgccgaatg ccggcttgga cccggtgaat tatcagaact tygcagtcac 180
gaacgacggg gtgatttt 198

<210> SEQ ID NO: 29
<211> LENGTH: 149
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 29
tcacganggt rynacmgcaa cwcgaccgcc acgtcasgcc gccgcgcacg aagatcaccg 60
tgcctgcncg atgggtcgtg aacggaatag aaygcagcgg tgaggtcaan ygcgaagccg 120
ggaaccaaat ccggtgaccg cgtcggcat 149

<210> SEQ ID NO: 30

```
<211> LENGTH: 210
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 30

ggacccgcca agcatcagcc ggtcaacagc cgccgccggt ggccaaagtt cgagcagccg      60

ccggtatcgt gctcggcccg gctagaccaa aaactttacg ccagcgcccg aagccacccg     120

actccaaggc ctcggcccgg ttgggttcgc acatgggtga gttctatatg ccctacccgg     180

gcacccggtt caaccaggaa accgtctcgc                                      210

<210> SEQ ID NO: 31
<211> LENGTH: 255
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 31

cagnccgctg ncccggaact gttccagcag ctacaagacc ttcgacaacg tngcgcgtca      60

acctgcantc gagcgcaacc tctcggtggc gctcaacgag tgttcgccgg cttcaacccg     120

ctggacccgc gaaacctcga cgtgtccccg ctgccttcgc tggccaagcg cgccgccgac     180

atcctgcgcc aggacgtggg cgggcaggtc gacattttcg atgtcaatgt gcccaccatc     240

cagtacgacc agagc                                                      255

<210> SEQ ID NO: 32
<211> LENGTH: 164
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 32

aaynccnggc crtcgacggt nccggttcnc rccaccggtc tatatccacc cgggtcnrca      60

ttmanantga ntmnccgccg gtgcggccgt cgagcgtgac ctggcatccc ctgagacgct     120

gctgggttgc cccggggagn tcgamantcg ggcatcgcac catc                      164

<210> SEQ ID NO: 33
<211> LENGTH: 237
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 33

acggacggca acgggatgcg acccgatccc accggtcgcc acgagggacg ctacttcgtc      60

gccgggcagc cganccgacc gtcngttcng cganggcgac ngccgaagcc gttgacccac     120

nttggtcagc agcagctgga tsagtcaggt gccgttggtg tttcgccgtc agcggtgtcg     180

gggtgggtgc gttctgggca ccgtcgactg tggtgggcgc tngcgggcgn tggtggc        237

<210> SEQ ID NO: 34
<211> LENGTH: 371
<212> TYPE: DNA
<213> ORGANISM: Mycobacterium tuberculosis
```

-continued

<220> FEATURE:
<221> NAME/KEY: Modified base
<223> OTHER INFORMATION: n represents a or g or c or t/u

<400> SEQUENCE: 34
cggatgctcg gcctccggta cccaactcga actcgcgccc acngcggacn gcagggccgc 60
ggttggcacc accagcgaca tcaatcangc aggatcccgc cacgttgcaa gacggcggca 120
atcttcgcct gtcgctcacc gactttccgc ccaacttcaa catcttgcac atcgacggca 180
acaacgccga ggtcgcggcg atgatgaaag ccaccttgcc gcgcgcgttc atcatcggac 240
cggacggctc gacgacggtc gacaccaact acttcaccag catcgagctg accaggaccg 300
ccccgcaggt ggtcacctac accatcaatc ccgaggcggt gtggtccgac gggaccccga 360
tcacctggcc g 371

<210> SEQ ID NO: 35
<211> LENGTH: 26
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 35
gagaactccg ggccganttt tggaca 26

<210> SEQ ID NO: 36
<211> LENGTH: 202
<212> TYPE: DNA
<213> ORGANISM: Mycobacterium tuberculosis

<400> SEQUENCE: 36
tgtcggtagc gttcgcgtcc atgattgctc ttgcaacgct gttgacgctt atcaatcaag 60
tcgtcggcac tccgtatatt cccggtggcg attctcccgc cgggaccgac tgctcggagc 120
tggcttcgtg ggtatcgaat gcggcgacgg ccaggccggt tttcggagat aggttcaaca 180
ccggcaacga ggaagcgcct tg 202

<210> SEQ ID NO: 37
<211> LENGTH: 319
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 37
ctanttttag aytnngtcgt gacatatccg ctgtacgcgt gggacggncc attattggat 60
aatgcgtgat aagcaccaca agaantgatt ncctatggat attgtcggta ncgttcgcgt 120
ccatgattgc tcttgcaacg ctgttgacgc ttatcaatca agtcgtcggc actccgtata 180
ttcccggtgg cgattctccc gccgggaccg actgctcgga gctggcttcg tgggtatcga 240
atgcggcgac ggccaggccg gttttcggag ataggttcaa caccggcaac gaggaagcng 300
ccttggcggc tcggggctt 319

<210> SEQ ID NO: 38
<211> LENGTH: 263
<212> TYPE: DNA
<213> ORGANISM: Mycobacterium tuberculosis

<400> SEQUENCE: 38

-continued ggtacttgtc gtcgatggac tcccggtctc gattcaggaa cagcgtcccg acgacaccgg 60
ctcccaccag cccgagaaac gccaccacgc cgcgagcgcc caccacagtc gacggtgcca 120
gaacgcacca cccgacacgt gacggcgaaa caccaacggc acctgactga tgccagctgc 180
tgctgaccaa gtgggcacgc tcggcgcgcc tcggaacgag tcgtcgctgc cgcgacgaag 240
acgcctcggc gacgtggatc ggg 263

<210> SEQ ID NO: 39
<211> LENGTH: 841
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 39
gcgttgcgcg ccctcgagca gtcnnttggc ggcgatcccg agacaatgat tcccgacatc 60
cggtacacac cgaaccccaa cgatgcgccg ggcggcccgc tggtagaaag gggaaatcgc 120
cagtgctgac tcgcttcatc cgacgccagt tgatcctttt tgcgatcgtc tccgtagtgg 180
caatcgtcgt attgggctgg tactacctgc gaattccgag tctggtgggt atcgggcagt 240
acaccttgaa ggccgacttg cccgcatcgg gtggcctgta tccgacggcc aatgtgacct 300
accgcggtat caccattggc aaggttactg ccgtcgagcc caccgaccag ggcgcacgag 360
tgacgatgag catcgccagc aactacaaaa tccccgtcga tgcctcggcg aacgtgcatt 420
cggtgtcagc ggtgggcgag cagtacatcg acctggtgtc caccggtgct ccgggtaaat 480
acttctcctc cggacagacc atcaccaagg gcaccgttcc cagtgagatc gggccggcgc 540
tggacaattc caatcgcggg ttggccgcat tgcccacgga gaagatcggc ttgctgctcg 600
acgagaccgc gcaagcggtg ggtgggctgg gacccgcgtt gcaacggttg gtcgattcca 660
ctcaagcgat cgtcggtgac ttcaaaacca acattggcga cgtcaacgac atcatcgaga 720
actccgggcc gattttggac agccaggtca acacgggtga tcagatcgac ngctgggcgc 780
gcaaattgaa caatctggcc gcacagaccg cgaccaggga tcagaacgtg cgaagcatcc 840
t 841

<210> SEQ ID NO: 40
<211> LENGTH: 209
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 40
gcggttggca ccaccagcga naatcagcag gndcccgcca cgttgcaaga cggcggcaat 60
cttcgcctgt cgctcaccga ctttccgccc aacttcaaca tcttgcacat cgacggcaab 120
aabgccgagg tcgcggcgat gatgaaagcc accttgccgc gcgcgttcat catcggaccg 180
gacggctcga cgacggtcga caccaacta 209

<210> SEQ ID NO: 41
<211> LENGTH: 167
<212> TYPE: DNA
<213> ORGANISM: Mycobacterium tuberculosis
<220> FEATURE:
<221> NAME/KEY: Modified base
<223> OTHER INFORMATION: n represents a or g or c or t/u -continued

<400> SEQUENCE: 41
agatcgtcag tgagcagaac cccgccaaac cggccgcccg aggtgttgtt cgagggctga 60
aggcgctgct cgcgacggtc gntgctggcc gtcgtcggga tcgggcttng gctcgcgctg 120
tacttcacgc cggcgatgtc ggcccgcgag atcgtgnatc atcggga 167

<210> SEQ ID NO: 42
<211> LENGTH: 221
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 42
ccagntcctc nnatatcgac accctcnacn aagaccgctt cgcgagatca acnctcagat 60
atncnnacta tcnccnntnc acgcacacct caacatnana naatngaact atngncttcg 120
cctcaccacc aaggttcagg ttancggctg ncgtttkctc tkcgccggct cgaacacgcc 180
atcgtgcgcc ggkacacccg gatgtttgac gacccgctgc a 221

<210> SEQ ID NO: 43
<211> LENGTH: 117
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 43
cggyccgnnc aayyygncgc gchncggygy agaggtcgny aaggtcgcca aggtaacgct 60
gatcgayggg nacangcaag tattggtgna cttcaccgtg ghthgcthgc tgtyagc 117

<210> SEQ ID NO: 44
<211> LENGTH: 385
<212> TYPE: DNA
<213> ORGANISM: Mycobacterium tuberculosis

<400> SEQUENCE: 44
gaacctcctc gcccgcgctt ggcctagcat taatcgactg gcacgacagt tgcccgactg 60
ggtacacggc atggacgcaa cgcgaatgaa tgtgagttag ctcactcatt aggcacccca 120
ggcgttgaca ctttatgctt ccggctcgtg tagttgtgtg ggaattgtgg agcggataac 180
aatttcgacg acgaggaaac agctgtagac atggattgac gaatttgaat acgactcact 240
ataggaattc gagctcggta cccggggatc ctctagagtc cttcgccgcg ggtcgccacc 300
atcagggcca gtgcgatcgc aagcgcgggg taccgggcgc catagtcttc agcatcggcg 360
tgttgaccgc agagaccgga cgggg 385

<210> SEQ ID NO: 45
<211> LENGTH: 285
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 45
cccgcagcag tacccgcagn cccacacccg ctatncgcag cccgaacagt tcggtgcaca 60
gcccacccna gctcggcgtg cccggtcagt acggccaata ccagcagccg ggccaatatg 120

-continued nccagccggn acagtnacgn ccagcccggc cagtacgcna ccgcccggtc agtaccccgg 180
gcaatacggc ccgtatgncc agtcgggtca ggggtcgaag cgttcggttg cggtgatcgg 240
cggcgtgatc gccgtgatgg ccgtgctgtt catcggcgcg gttct 285

<210> SEQ ID NO: 46
<211> LENGTH: 186
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 46
gcncgtgncc gtgccgcccg gttgaacgtg agcngctgnc natngcccca gccgagacga 60
gaacgtcccc gaggagtatg cagactggga agacgccgaa gactatgacg actatgacga 120
ctatgaggcc gcagaccagg aggccgcacg gtcggcatcc tggcgacggc ggttgcgggt 180 ncggtt 186

<210> SEQ ID NO: 47
<211> LENGTH: 409
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 47
gtcgctgaat gtgttgtcgg agaccgtnga tcagacctat ccgcacctga gcgccgccnt 60
cgacgggntg gctaagttct ccgacaccat cggcaagcgc gacgagcaga ntcacgcacc 120
tactagccca ggccaaccag gtggccagca tcctgggtga tcgcagtgag caggtcgacc 180
gcctattggt caacgctaag accctgatcg ccgcgttcaa cgagcgcggc cgcgcggtcg 240
acgccctgct ggggaacatc tccgctttct cgncccaggt gcaaaacctt natcaacgac 300
aacccgaacc tgaaccatgt gctcgnnnag ctgcgcatcc tcancgacct gttggtcgac 360
cgcaaggagg atttggctga aaccctgacg atcttgggca gattcagcg 409

<210> SEQ ID NO: 48
<211> LENGTH: 464
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 48
agnccgtgca ctggaacttc ggctcgatgt ctccgatgtg gacggcaagc tgatgatctc 60
ccggttggan gtcgattcga tgasaaatgn cttggcggct ggtggtgttc gatgncctgg 120
caccactggc cacgatcgcc gccntggccg cgatcggcgn cttngctcgg ctggcccctg 180
tggtgggttt cgacgtgctc ggtgttggtg ctgctggtgg tcgaaggtgt ggcaatcaac 240
nttctggctg ttgcgtcgtg attcggtaac cgtcggtacc gacgacgatg cgcccgggct 300
gcgactggcc gttgtcttcc tgtgcgccgc cgcgatctcg gcggcggtgg tgactgggta 360
cctgcgctgg acgacaccgg accgcgactt caatcgggat tcccgggaag tggtgcatct 420
tgccacgggg atggccgaga cggtcgcgtc attctccccg agcg 464

-continued

<210> SEQ ID NO: 49
<211> LENGTH: 423
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 49
gtccaaggcc gtagcccacc tcctggaagt cgtaccacgt cgactcgacc aggacggctg 60
cantcagcna cttcgtcaac ccggcgatca tcaacntgca cctacggcag tgtgnacgca 120
ccccggacca tcgcactggc cggggnttca cacgccgaac actgnctgac cgcactggat 180
ctgctnggtc gcatgcacca cttcaaggtg gtgacgtacc tcaaaatggg ttkcccgttg 240
tccaccgagg aagtcccgct gatncatggg caataacgct ccctatccgc agtgtcacca 300
gtgggtgcaa gcggcgatgg ccaagttggt cgctgaccac cccgactacg ttttcacaac 360
ctcgactcga ccgtggaaca tcaaacccgg cgatgtgatg ccagcaacct atgtcgggat 420
ctg 423

<210> SEQ ID NO: 50
<211> LENGTH: 279
<212> TYPE: DNA
<213> ORGANISM: Mycobacterium tuberculosis

<400> SEQUENCE: 50
cggtcgagcc gatgaacgtc tgcagttcac cgcaaccacg ctcagcggtg ctcccttcga 60
tgcgcaagcc tgcaaggcaa tgccgcggtg ttgtggttct ggacgccgtg gtgcccgttc 120
tgcaactgtc agaagccccc agccgcagcc aggtagcggc cgctaatccg gcggtcacct 180
tcgtcggaat cgccacccgc gccgacgtcg gggcgatgca gagctttgtc tcgaagtaca 240
acctgaattt caccaacctc aatgacgccg atggtgtga 279

<210> SEQ ID NO: 51
<211> LENGTH: 331
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 51
cggcccgscg gcgccntggt gaagcttggm gmmtgggtgn agcgcagctg cccaccacac 60
ggraccnngg tgcggacgcg gntgacgcgc ctggtggtca gcatcgtggc cggtctgctg 120
ttgtatgcca gcttcccgcc gcgcaactgc tggtnggcgg cggtggttgs gctncgcatt 180
gctggcctgg gtgctgaccc accgcgcgac gacaccggtg ggtgggctgg gctacggcct 240
gctattcggc ctggtgttct acgtctcgtt gttgccgtgg atcggcgagc tggtgnnccc 300
cgggccctgg ttggcactgg cgacgacgtg c 331

<210> SEQ ID NO: 52
<211> LENGTH: 507
<212> TYPE: DNA
<213> ORGANISM: Mycobacterium tuberculosis

<400> SEQUENCE: 52
tgtattcccg tcgatgcgtt gctgcaggta ggccttgaaa tcgttggggg tcacgacgcg 60
gacctcgaag ttcatcatcg agtgatacgt gccacacatc tcggcgcagt ggcccacgaa 120

-continued tgctccggtc ttggtgattt cttcgatctg gaagacgttg accgagttgt ttgccaccgg 180
gttaggcatc acgtcacgct tgaacaagaa ctccggcacc cagaatgcgt gtatcacatc 240
ggctgaggcc atttggaatt cgatacgctt gccggacggc agcaccagca ccggaatttc 300
ggtgctggtg cccaacgtct cgaccttgtc gaaattcagg taggtccggt cctcggtgtt 360
gagcccgcgc accggcccga ccagctcttc gccgtacttg tccttgccct ctggcttgga 420
aaccatggcg cgcttgcgct ccggatcggc accatcatag gtcagtgtgc cgtctttgaa 480
gttcaccctt tgatagccaa acttcca 507

<210> SEQ ID NO: 53
<211> LENGTH: 293
<212> TYPE: DNA
<213> ORGANISM: Mycobacterium tuberculosis

<400> SEQUENCE: 53
ccacacaaca caaatctacg tcgtaatgca gtcgtaagtc catccgacgt cgatggcaag 60
gacagcaccc gacggccaac ggcatataca tcgtcggctc gccggtcaca agcacatcat 120
catggactcg tccactacgg cgtacccgtc aactcgccca acggatatcg caccgatgtc 180
gactggccac ccagatctcc tacagcggtg tcttcgtgca ctcagcgccg tggtcggtgg 240
gggctcaggg ccacaccaac accagccatg gctgcctgaa cgtcagcccg agc 293

<210> SEQ ID NO: 54
<211> LENGTH: 820
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 54
cgccgccggc gngcgctacc ggtgcgggag ggtacaccca agcantccgg gaccggccgt 60
cycgccggga acgccgtgct cctacacacc ggcggcgggc gcgttgccac ggcccgacac 120
cccactaccc tgncgcgggc gccaccgttg gcccgttcgg tggacccgac ttcccggcac 180
cgctcgatgt ccagccgtcg ccgcctaatc ccgatgggcc gccgccgacg ccgggcatcc 240
taagtgctgg gcggccgggc gagccggctc cggctgttcc ggncataccg atgccsctgc 300
cgccgaacnn nnnnnnnnnt gcacgcaccc aaccgcttga gccgtttcct gacgggacgg 360
gaggtagcaa ccaatgagca ccatcttcga catccgsagc ctgcgactgy cgaaactgtc 420
tgcaaaggta gtggtcgtcg gcgggttggt ggtggtcttg gcggtcgtgg ccgctgcggc 480
cggcgcgcgg ctctaccgga aactgactac cactaccgtg gtcgcrtatt tnctstgagg 540
cgctcgcgct gtacccagga gacaaagtcc agatcatggg tgtgcgggtc ggttctatcg 600
acaagatcga gccggccggc gacaagatgc gagtcacgtt gcactacagc aacaaatacc 660
aggtgccggc cacgnctacc gcgtcgatcc tcaaccccag cctggtggcc tcgcgcacca 720
tccagctgtc accgccgtac accggcggcc cggtcttgca agacggcgcg gtgatcccaa 780
tcgagcgcac ccaggtgccc gtcgagtggg atcagttgcg 820

<210> SEQ ID NO: 55
<211> LENGTH: 117
<212> TYPE: DNA
<213> ORGANISM: Mycobacterium tuberculosis

<400> SEQUENCE: 55

-continued cagccacctc gttcgccgcc gacatcgact atcagccgac ccggccactg ctgacctgat 60
cgccaacagc tggaggccct accggctgca gttcaattca cccgctgcgg gtcggcg 117

<210> SEQ ID NO: 56
<211> LENGTH: 242
<212> TYPE: DNA
<213> ORGANISM: Mycobacterium tuberculosis

<400> SEQUENCE: 56
aggtgtcgtg cttcatgcct ggcgcccaat ccagtttcta caccgactgg tatcaccctt 60
cgcagacaaa cggccagaac tacacctaca agtgggagac cttccttacc acacagatgc 120
ccgcctggct acaggccaac aaggcgtgtc ccccacaggc aacgcggcgg tgggtctttc 180
gatctcgggc ggttccgcgc tgaccctggc cgcgtactac ccgcagcagt tcccgtacgc 240
cg 242

<210> SEQ ID NO: 57
<211> LENGTH: 345
<212> TYPE: DNA
<213> ORGANISM: Mycobacterium tuberculosis

<400> SEQUENCE: 57
tgctgcagat agccaaggat cccgaggtcg tgattgatat cacgtctttc cagtggaatt 60
ggaagtttgg ctatcaaagg gtgaacttca aagacggcac actgacctat gatggtgccg 120
atccggagcg caagcgcgcc atggtttcca agccagaggg caaggacaag tacggcgaag 180
agctggtcgg gccggtgcgc gggctcaaca ccgaggaccg gacctacctg aatttcgaca 240
aggtcgagac gttgggcacc agcaccgaaa ttccggtgct ggtgctgccg tccggcaagc 300
gtatcgaatt ccaaatggcc tcagccgatg tgatacacgc attct 345

<210> SEQ ID NO: 58
<211> LENGTH: 262
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 58
cngactccaa cnagtgcgnt caancngntg tnccngacaa gaaggttcct acatccgcaa 60
ntcggtgnaa ngccactgtg gatgcctacg acggaacggt cacgctgtac caacaggacg 120
naaaaggatc cggtgctcaa ggcctggatg caggtcttcc ccggcacggt aaagcctaag 180
agcgacattg cgccggagct tgccgagcan ctgcggtatc ccgaggacct gttcaaggtg 240
cagcgcatgt tgttggccaa at 262

<210> SEQ ID NO: 59
<211> LENGTH: 241
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 59
ccaccannna acrrcacagc tccggccrrc cgtncgcagg ccacccgcan cgtagtgctc 60
aaattcttcc aggacctcgg tggggyacat ccgtccacct ggtacaaggc cttcaactac 120
aacctcgcga cctcgcagcc catcaccttc gacacgttgt tcgtgcccgg caccacgcca 180

-continued ctggacagca tctaccccat cgttcagcgc gagctggcac gtcagaccgg tttcggtgcc 240
g 241

<210> SEQ ID NO: 60
<211> LENGTH: 243
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 60
ccggcggatc tgcgtgacga ntgtatncca cggnactacc cgcggtcctt cctcnantnc 60
cgccggncca gncgcagnct ncngatgtcc ngctataacc tgcgcgatcg ccgccgggct 120
gcccgacaac acggtgngcg ccgccgctgc ttccgccaat tctgggtgnc ggcatnccgg 180
cagcgcccgg cccagcactg agagggggac gttgatgcgg tggccgacgg cgtggctgct 240
ggc 243

<210> SEQ ID NO: 61
<211> LENGTH: 2348
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 61
gcgctgtcat tcggacttcg gaccgcgttg gcggtggtgc tgatcatgaa nctacgacgg 60
cgccaccggc agcttcccgt catgggtgct ctatccctgt gcgctggcca tgatggtgtt 120
ctcgaagtcg ttcagcgtgc tgcgcagcgc agtgacaccg agggtgatgc cgccaaccat 180
cgacttggtc cgggtcaact cacggctgac cgtgttcggc ctgctcggcg gcaccatcgc 240
tggtggcgcg attgcggccg gagtcgaatt cgtctgcacc cacctgttcc agctgccggg 300
cgcgttgttc gtcgtcgtcg cgatcaccat cgctggcgct tcgctgtcga tgcgcattcc 360
gcgctgggtc gaggtgacca gcggtgaggt cccggccaca ttgagctacc accgggatag 420
gggcagacta cggcgacngc tggccggagg aagtcaagaa cctcggcgga acactccgac 480
aaccgttggg ccgcaacatc attacctccc tgtggggtaa ctgcaccatc aaggtgatgg 540
tcggctttct gttcttgtat ccggcgtttg tcgccaaggc gcacgaagcc aacgggtggg 600
tgcaattggg catgctgggc ctgatcggcg cggcggccgc ggtcggcaac ttcgccggca 660
atttcaccag cgcacgcctg cagctaggca ggccagctgt gctggtngtg cgctgcaccg 720
tgctagttac cgtgttagcc atcgcggccg cggtggccgg cagcctggca gcgacagcga 780
ttgccaccct gatcacggca gggtccagtg ccattgctaa agcctcgctg gacgcctcgt 840
tgcagcacga cctgcccgag gagtcgcggg catcggggtt tgggcgttcc gagtcgactc 900
ttcagctggc ctgggtgctg ggcggcgcgg tgggcgtgtt ggtgtacacc gagctgtggg 960
tgggcttcac tgcggtgagc gcgctgctga tcctgggtct ggctcagacc atcgtcagct 1020
tccgcggcga ttcgctgatc cctggcctgg gcggtaatcg gcccgtgatg gccgagcaag 1080
aaaccacccg tcgtggtgcg gcggtggcgc cgnagtgaag cgcggtgtcg caacgctgcc 1140
ggtgatcctg gtgattctgc tctcggtggc ggccggggcc ggtgcatggc tgctagtacg 1200
cggacacggt ccgcagcaac ccgagatcag cgcttactcg cacgggcacc tgacccgcgt 1260

-continued

```
ggggccctat ttgtactgca acgtggtcga cctcgacgac tgtcagaccc cgcangcgca   1320

gggcgaattg ccggtaagcg aacgctatcc cgtgcagctc tcggtacccg aagtcatttc   1380

ccgggcgccg tggcgtttgc tgcaggtata ccaggacccc gccaacacca ccagcacctt   1440

gtttcggccg gacacccggt tggcggtcac catccccact gtcgacccgc agcgcgggcg   1500

gctgaccggg attgtcgtgc agttgctgac gttggtggtc gaccactcgg gtgaactacg   1560

cgacgntccg cacgcggaat ggtcggtgcg ccttatcttt tgacgaggcc gcggctcgac   1620

gggacgctta agcgcggtcg gcgccaacgg tccgaagagc cgccgacacc cggggcacat   1680

cggcgcatca tggaactgtg cggatcggag tcggggtttg caccacgccc gacgcgcggc   1740

aggccgcggt ggaggctgcg ggccaggcgc gcgacgagct ggcgggtgag gcgccgtcgc   1800

tggcggtgtt gcttggatcg cgtgcacaca ccgaccgggc tgccgacgtc ctgagcgcgg   1860

tgctgcagat gatcgayccg cccgcgcttg tcggttgcat cgcccaggcc atcgtcgccg   1920

gccgccacga gatcgaggac gagcccgcgg tggtggtgtg gctggcgtcc ggcttggccg   1980

ccgagacatt ccagctggac tttgtccgta ccggctcggg tgccctgatc accggttatc   2040

ggttcgaccg caccgcccgg gatctgcatc tgctgctgcc ggacccgtac acattcccgt   2100

cgaacctgct catcgagcac cccaacaccg acctgccggg caccgccgtc gtgggcggcg   2160

ntggtgagcg gcgggcgccg gcggggcgac acccggctgt tccgcgatca cgacgtgctc   2220

acctccggcg tcgtcggcgt gcgcctgccc gggatgcgcg gtgtmccggt cgtgtcgcag   2280

ggttgccggc cgatcggcta cccatacatc gtcaccggcg cggacggcat actgatcacc   2340

gagctcgg                                                            2348
```

<210> SEQ ID NO: 62
<211> LENGTH: 821
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 62

```
cgttacccgc tttacaccac cgccaaggcc aacctgaccg cgctcagcac cgggctgtcc     60

agctgtgcga tggccgacga cgtgctggcc gagcccgacc ccaatgccgg catgctgcaa    120

ccggttccgg gccaggcgtt cggaccggac ggacgctggg cggtatcagt cccgtcggct    180

tcaaacccga gggcgtgggc gaggacctca agtccgancc cggtggtctc caaacccggg    240

ctggtcaact ccgatgcgtc gcccaacaaa cccaacgccg ccatcaccga ctccgcgggc    300

accgccggag ggaagggccc ggntcgggat ncaacgggtt gcnacgcggc gctgccgttc    360

nggattggac ccggcacgta ccccggtgat gggcagctac ggggagaaca acctggccgc    420

cacggccacc tcggcctggt accagttacc gccccgcagc ccggaccggc cgctggtggt    480

ggtttccgcg gccggcgcca tctggtccta caaggaggac ggcgatttca tctacggcca    540

gtccctgaaa ctgcagtggg gcgtcaccgg cccggacggc cgcatccagc cactggggca    600

ggtatttccg atcgacatcg gaccgcaacc cgcgtggcgc aatctgcggt ttccgctggc    660

ctgggcgccg ccggaggccg acgtggcgcg cattgtcgcc tatgacccga acctgagccc    720

tgagcaatgg ttcgccttca ccccgccccg ggttccggtg ctggaatctc tgcagcggtt    780

gatcgggtca gcgacaccgg tgttgatgga catcgcgacc g                        821
```

<210> SEQ ID NO: 63

-continued

<211> LENGTH: 479
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 63
gccagccgtg atcggctgay cggncagntg atcaccaacc tcaacgtggt gctgggcntc 60
gctggncgct cacacngatc ggttggacca gscggtgacg tcgctatcag cgttgattca 120
ccggctcgcg caacgcaaga ccgacatctc caacgccgtg gcctacacca acgcgccgcc 180
ggctcggtcg ccgatctnct gtcgcaggct cgcgcnncgt tggcgaangt ggttcgcgag 240
accgatcggg tggccggcat cgcggccgcc gaccacgact acctcgacaa tctgctcaac 300
acgctgccgg acaaatacca ggcgctggtc cgccagggta tgtacggcga cttcttcgcc 360
ttctacctgt gcgacgtcgt gctcaaggtc aacggcaagg gcggccagcc ggtgtacatc 420
aagctggccg gtcaggacan gcnggcggtg cgcgccgaaa tgaaatcctt cgccgaacg 479

<210> SEQ ID NO: 64
<211> LENGTH: 481
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 64
kgtctcgcgn ccttaacatc cggtcgcccc ancggtaatc tgcctgtgga tgccgtccgg 60
aantataagc aaatggccag gagtgcgtga cgcagttatg gctcggtata gttccgttnt 120
tgccccggac tgggggcgtg aggtggaact aatggcggtg tcgggtgata tttccgacgg 180
caagcgacca tataggtgga tcgacggcaa taaasacacg ctctggccac gtttcttggc 240
ggggaaaggg gtgatgctat cggagccaat ggtatcgcga caacacttgc agatgccgcc 300
aaggccgatc acgctaatga cggattcggg gccacaaacg ttccccgttc tggcggtttt 360
ctctgactac acctcagatc aaggtgtgat tttgatggat cgcgccagtt atcgggccca 420
ttggcaggat gatgacgtga cgaccatgtt tcttttttttg gcnatncggg tgcgaatagc 480
g 481

<210> SEQ ID NO: 65
<211> LENGTH: 469
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 65
ggcgaggtca gtgaagccga ggaagcggaa aggagcgccc aatacggaac cgcctctccc 60
cgcgcgttgg ccgattcatt aaatgcagct ggcacgacag gtttcccgac tggaamgcgg 120
gcagtgagcg caasgcaatt aatgtgagtt agctcactca ttaggcaccc caggctttac 180
actttatgct tccggctcgt atgttgtgtg gaattgtgag cggataacaa tttcacacag 240
gaaacagcta tgacatgatt acgaatttaa tacgactcac tatagggaat tcgagctcgg 300
tacccgggga tcctctagag tcgcttcggt tggcggcgac cagcagtgga tccacggtgg 360
ccgcccgcgc ggcdtcatac accgccgcgg cctccttggc ctgtgcggcc sgcttagcgc 420

-continued gcgtgttgct gccgtgctta gccanctggc atagggggct gccgcgcgc 469

<210> SEQ ID NO: 66
<211> LENGTH: 291
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 66
caggttcgac tgatctagct gnrrrccara ccggcacnag ncgacantta ccantacctg 60
acanacagnc cgntcnagcc aanccgnann naggangcag nagnaacagg cagatgcatc 120
taatgatacc cgcggagtat atctccaacg tgatatatga aggtccgcgt gctgactcat 180
tgtatgccgc cgaccagcga ttgcgacaat tagctgactc agttagaacg actgccgagt 240
cgctcaacac cacgctcgac gagctgcacg agaactggaa aggtagtttc a 291

<210> SEQ ID NO: 67
<211> LENGTH: 1306
<212> TYPE: DNA
<213> ORGANISM: Mycobacterium tuberculosis

<400> SEQUENCE: 67
gtgatacagg aggcgccaac agtgacacct cgcgggccag gtcgtttgca acgcttgtcg 60
cagtgcaggc ctcagcgcgg ctccggaggg cctgcccgtg gtcttcgaca gctggcgctc 120
gcagcaatgc tgggggcatt ggccgtcacc gtcagtggat gcagctggtc ggaagccctg 180
ggcatcggtt ggccggaggg cattaccccg gaggcacacc tcaatcgaga actgtggatc 240
ggggcggtga tcgcctccct ggcggttggg gtaatcgtgt ggggtctcat cttctggtcc 300
gcggtatttc accggaagaa gaacaccgac actgagttgc cccgccagtt cggctacaac 360
atgccgctag agctggttct caccgtcata ccgttcctca tcatctcggt gctgttttat 420
ttcaccgtcg tggtgcagga gaagatgctg cagatagcca aggatcccga ggtcgtgatt 480
gatatcacgt ctttccagtg gaattggaag tttggctatc aaagggtgaa cttcaaagac 540
ggcacactga cctatgatgg tgccgatccg gagcgcaagc gcgccatggt ttccaagcca 600
gagggcaagg acaagtacgg cgaagagctg gtcgggccgg tgcgcgggct caacaccgag 660
gaccggacct acctgaattt cgacaaggtc gagacgttgg gcaccagcac cgaaattccg 720
gtgctggtgc tgccgtccgg caagcgtatc gaattccaaa tggcctcagc cgatgtgata 780
cacgcattct gggtgccgga gttcttgttc aagcgtgacg tgatgcctaa cccggtggca 840
aacaactcgg tcaacgtctt ccagatcgaa gaaatcacca agaccggagc attcgtgggc 900
cactgcgccg agatgtgtgg cacgtatcac tcgatgatga acttcgaggt ccgcgtcgtg 960
acccccaacg atttcaaggc ctacctgcag caacgcatcg acgggaakac aaacgccgag 1020
gccctgcggg cgatcaacca gccgcccctt gcggtgacca cccacccgtt tgatactcgc 1080
cgcggtgaat tggccccgca gcccgtaggt taggacgctc atgcatatcg aagcccgact 1140
gtttgagttt gtcgccgcgt tcttcgtggt gacggcggtg ctgtacggcg tgttgacctc 1200
gatgttcgcc accggtggtg tcgagtgggc tggcaccact gcgctggcgc ttaccggcgg 1260
catggcgttg atcgtcgcca ccttcttccg gtttgtggcc gcggat 1306

<210> SEQ ID NO: 68
<211> LENGTH: 728
<212> TYPE: DNA

-continued

<213> ORGANISM: Mycobacterium tuberculosis
<220> FEATURE:
<221> NAME/KEY: Modified base
<223> OTHER INFORMATION: n represents a or g or c or t/u

<400> SEQUENCE: 68
ggtgcctgcc atcggttcgc tggccacgct ggcatctttg gtctgttaga ggtatccgcg 60
cggatggcca gtcctgttgg cggggnttgt cgccacgatt gccgcccgcg ctgaancccg 120
acgacgccga tgccctgccc accacggatc ggctgaccac ccgagcgaac cgtgcagatg 180
cttggttgac gagcctgctg gcgnccttcg cggcctcggc gaccatcggt gccatcggaa 240
ccgccgtcgc aacccacggc atccacagst ccagcatngg cggtatcgcg ttggccgncg 300
tcaccggtgc gctgctgctg ctacgagcac gttcagcaga caccagaagg tcactggtgt 360
ttgccatctg tggaatcacc accgttgcaa cggcattnta ccgtcgccgc ggatcgggct 420
ctggaacacg ggccgtggat tgccgcgctg accgccatgc tggnccgccg tggcaatgtt 480
tttgggcttc gtcgctcccg cgttgtcgct ctcgcccgtc acgtaccgca ccatcgaatt 540
gctggagtgt ctggcgctga tcgcaatggt tccattgacc gcttggstat gcggcgccta 600
caggcgcgtt cgccacctcg acctgacatg gacatgacca cngtcccgta ccctgcgcct 660
gctggtggta tcagcgctcg cgacgctgtc tgggttggga acgccggttg cgccacgcgg 720
tttcgccg 728

<210> SEQ ID NO: 69
<211> LENGTH: 1028
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 69
gktcncggtg atgtcgaccg tcggcacgac gagcgaaacc tcaccggtcg acagtgtctg 60
cccgaggccg cagccgacgt gcccccggag accgcgcgcc aacacggtgc cgtacatgta 120
gcccgcacgg cgcatcatcg ccgagccggc gtagatgttt tcctgcacgg cgtgcgcggt 180
gaacccntcc ggcgccagca ccgccacctt tcccgcgtcc acgtcggcct gggtggtgac 240
gccgagcacc ccaccgaaat gatcgacatg gctgtgggtg tagatgaccg scgaccacgg 300
ggcggtcggc tccgcggtgg gcgcgataca agtccagcgc ggcggcggcc acctcggtgg 360
acaccaacgg gtcgatgacg atcagcccag tgtcaccctc aacgaagctg atattggaga 420
tatcgaatcc gcggacctga tagatgcccg gcaccacctg gtagaggccc tgtttcgcgg 480
tcagctggga ttgccgccac aggctgggat gcaccgatgt cggcgcggca ccgtcgagaa 540
acgagtacgc gtcgttgtcc cacaccacgc gaccatcggc agccttgatc acacacgggg 600
acagcgcggc aatgaatccg cgatcggcgt cgtcgaaatc cgttgtgtca tgcaacggta 660
acgagtgttc accgtgtgcc gcctggatga cggcagtngg gaggtttgtg ttccatcggc 720
actacattgc cactactacg gtgcacgccg gtagatgccg ttggcgaacc acgctaccga 780
ccagaaagag agaattttcc gccgcaccta gacctcgggc cctcntaacg cgcatactgc 840
cgaagcggtc ctcaatgccg atggaccgct acgacaggca aaggagcaca gggtgaagcg 900
tggactgacg gtcgcggtag ccggagccgc cattctggtc gcaggtcttt ccggatgttc 960
aagcaacaag tcgactacag gaagcggtga gaccacgacc gcgngcaggc acgacgcaag 1020
ccccggcg 1028

-continued

<210> SEQ ID NO: 70
<211> LENGTH: 780
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 70
agatcaacac catcaccagt gcggtcatcg agttgctgca gggcnagggt ggtccgttgg 60
cgaacgtgct cgccgcyacc ggtgccttct cggcggcgct gggcgcacgc gaccagctga 120
tcggcgaggt aatcaccaac ctcaacgcgg tgctggcgac cgtcgatgca aagagcgcgc 180
aatttntcgg ccagtgtcga ccagctgcag cagctggtca gcggcctggc caagaaccgg 240
gatccgatcg cgggcgccat ttcgccgctg gcgtcgacga cgacggatct tacggaactg 300
ttgcggaatt cgcgccggcc gctgcaaggc atcctggaaa acgcccggcc gctggctacc 360
gagctggaca accgaaaggc cgaggtcaas aacgacatcg agcagctcgg cgaggactac 420
ctgcgcctgt ccgcgctggg cagttacgga gcattcnttc aacatctact tctgctcggt 480
gacgatcaag atcaacggac cggccggcag cgacatcctg ctgccgatcg gcggccagcc 540
ggatcccagc aaggggaggt gcgcctttgc taaataggaa gccaagtagc aaacacgaac 600
gcgacccgnt ccgcaccggc atcttcggcc tggtgctggt gatctgcgtc gtcctgatcg 660
cattcggcta cagcgggttg cctttctggc cacagggcaa aacctacgac gcgtatttca 720
ccgacgccgg tgggatcacc cccggtaact cggtttatgt ctcgggcctc aaggtgggcg 780

<210> SEQ ID NO: 71
<211> LENGTH: 689
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 71
ctatccgcaa ggcttcgcag acgctcggct gnaccgcaga atcgcggtgc acccacgatt 60
gccagtagcg cgggcccact cgtgcctact acacttcgtc gtagccaaat catcggcccc 120
gtagtatctc cggagatgac agatgaatgt cgtcgacatt tcgcggtggc agttcggtat 180
caccaccgtc tatcacttca ttttcgtnac cgctgaccat cggcctggcc ccngctgatc 240
gcggtcatgc aaactgctgt nggtcgtcac cgataacccc gcctggtatc gcctcaccaa 300
attcttcggc aaattgttcc tgatcaactt tgccatcggc gtggcgaccg gaatcgtgca 360
ggaatttcag ttcggcatga actggagcga gtactcccga ttcgtcggcg atgtcttcgg 420
cgccccgctg gccatggagg gcctggcggc cttcttcttc gaatccacct tcatcgggtt 480
gtggatcttc ggctggaaca ggctgccccg gctggtgcat ctggcctgca tctggatcgt 540
cgcaatcgcg gtcaacgtgt ccgcgttctt catcatcgng gcaaactcct tcatgcagca 600
tccggtcggc gcgcactaca acccgaccac cgggcgtgcc gagttgagca gcatcgtcgt 660
gcctgctgac caacaacacc gcacaggcg 689

<210> SEQ ID NO: 72
<211> LENGTH: 274
<212> TYPE: DNA
<213> ORGANISM: Mycobacterium tuberculosis -continued

<400> SEQUENCE: 72
ccgcagcacc gaggcaagca tcgcacccgt cgattcccgc catcccggcg acatgatggt 60
catgtccgac accgacgccc gcacctcgct tcccgagttg accgcgctgc gcgtggacgc 120
cgcaacggat gcgtcggttc attcgatccc ggctcgaaat tggccatggc gaacgcatct 180
tgctgtgatg gttcgggcag tagatctcca ctgccgcact gataaactcg ggtcatggtc 240
gtcgtgaggc ggacagggta gaggcgcatg accg 274

<210> SEQ ID NO: 73
<211> LENGTH: 252
<212> TYPE: DNA
<213> ORGANISM: Mycobacterium tuberculosis

<400> SEQUENCE: 73
gtgatgcctt ccagcattgg attggtcgtc ggttcgatgc tgtggcgaca gataaaccgc 60
ctgttcgggg tgcgtggcct ctgctgggca gcgcactgct caacgccgct ctgcgctgct 120
gtgcatggtg gccgagtcgt gtgggcagtg ggttcacgcc tgggcgtact tcacggcgtt 180
cctgctggct acggtggccg ctcaaacggt ggtcgccgca tcgatatcgt ggatcagcgt 240
cctcgcgccc ga 252

<210> SEQ ID NO: 74
<211> LENGTH: 160
<212> TYPE: DNA
<213> ORGANISM: Mycobacterium tuberculosis

<400> SEQUENCE: 74
ggcgccgccg tcgtgctggc cgcccggccc ggtgggggtg ccggccagcg tggttccgcc 60
agtggccgcg ccgaacgtat tggccggcgt cctcgagcac gacaacgacg ggtcgggggc 120
ggcggtgctg gccgcgctgg ccaagctgcc acccggtggt 160

<210> SEQ ID NO: 75
<211> LENGTH: 401
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 75
atcagccgcg ggtcgacgcc gccgatgacc tcgacgtcgt cgtcgtcgct gccggtactc 60
aatccaatca ccatcctctt acgcaccttc taggagtgtg ttgctgcggc agtgccgngc 120
cattcgtaga ttcgggcctc gccgttgtcg tagatcttcg cccacgacct cgatgtctct 180
aacgacacta gtccgtccgg cacngcaaan ccccgcaccg tcggagtgct ggtcaggnta 240
tagncggtac aggnggactt ggwwggcctc gagtanccga ggwwcgntct ncccgttgcg 300
gncataggcc agaagatgaa ccggtgtaga ccgggcctgt tgcgagggtc gtagtcgtag 360
gtcccagagg tgtcggacgc ccaggttaat acacagcgtg c 401

<210> SEQ ID NO: 76
<211> LENGTH: 248
<212> TYPE: DNA
<213> ORGANISM: Mycobacterium tuberculosis

<400> SEQUENCE: 76
gcagacctct ggccgctggt ggtgctgggt acctgcgctg gcgacaccgg accgcagacc 60

-continued

```
gtcaatcggg actcccggga acgtggtgcc atcttgccac ggggatggcc gacgcggctc    120

gtcattctcc ccgagcgcac cggccgccgc tgttgaccgg gccgcggcga ctgatggtgc    180

ccgcacacgc gggcgggttc aaggagcaat acgccaagtc cagcgccgct ctcgcacggc    240

gcggtgtt                                                             248


<210> SEQ ID NO: 77
<211> LENGTH: 17
<212> TYPE: PRT
<213> ORGANISM: Mycobacterium tuberculosis

<400> SEQUENCE: 77

Val His Leu Ala Thr Gly Met Ala Glu Thr Val Ala Ser Phe Ser Pro
  1               5                  10                  15

Ser


<210> SEQ ID NO: 78
<211> LENGTH: 17
<212> TYPE: PRT
<213> ORGANISM: Mycobacterium tuberculosis

<400> SEQUENCE: 78

Arg Glu Val Val His Leu Ala Thr Gly Met Ala Glu Thr Val Ala Ser
  1               5                  10                  15

Phe


<210> SEQ ID NO: 79
<211> LENGTH: 17
<212> TYPE: PRT
<213> ORGANISM: Mycobacterium tuberculosis

<400> SEQUENCE: 79

Arg Asp Ser Arg Glu Val Val His Leu Ala Thr Gly Met Ala Glu Thr
  1               5                  10                  15

Val


<210> SEQ ID NO: 80
<211> LENGTH: 17
<212> TYPE: PRT
<213> ORGANISM: Mycobacterium tuberculosis

<400> SEQUENCE: 80

Asp Phe Asn Arg Asp Ser Arg Glu Val Val His Leu Ala Thr Gly Met
  1               5                  10                  15

Ala


<210> SEQ ID NO: 81
<211> LENGTH: 17
<212> TYPE: PRT
<213> ORGANISM: Mycobacterium tuberculosis

<400> SEQUENCE: 81

Ile Ser Ala Ala Val Val Thr Gly Tyr Leu Arg Trp Thr Thr Pro Asp
  1               5                  10                  15

Arg


<210> SEQ ID NO: 82
<211> LENGTH: 17
<212> TYPE: PRT
<213> ORGANISM: Mycobacterium tuberculosis
```

-continued

<400> SEQUENCE: 82

Ala Val Val Phe Leu Cys Ala Ala Ala Ile Ser Ala Ala Val Val Thr
1 5 10 15

Gly

<210> SEQ ID NO: 83
<211> LENGTH: 17
<212> TYPE: PRT
<213> ORGANISM: Mycobacterium tuberculosis

<400> SEQUENCE: 83

Val Thr Asp Asn Pro Ala Trp Tyr Arg Leu Thr Lys Phe Phe Gly Lys
1 5 10 15

Leu

<210> SEQ ID NO: 84
<211> LENGTH: 17
<212> TYPE: PRT
<213> ORGANISM: Mycobacterium tuberculosis

<400> SEQUENCE: 84

Ala Trp Tyr Arg Leu Thr Lys Phe Phe Gly Lys Leu Phe Leu Ile Asn
1 5 10 15

Phe

<210> SEQ ID NO: 85
<211> LENGTH: 17
<212> TYPE: PRT
<213> ORGANISM: Mycobacterium tuberculosis

<400> SEQUENCE: 85

Lys Phe Phe Gly Lys Leu Phe Leu Ile Asn Phe Ala Ile Gly Val Ala
1 5 10 15

Thr

<210> SEQ ID NO: 86
<211> LENGTH: 17
<212> TYPE: PRT
<213> ORGANISM: Mycobacterium tuberculosis

<400> SEQUENCE: 86

Phe Leu Ile Asn Phe Ala Ile Gly Val Ala Thr Gly Ile Val Gln Glu
1 5 10 15

Phe

<210> SEQ ID NO: 87
<211> LENGTH: 17
<212> TYPE: PRT
<213> ORGANISM: Mycobacterium tuberculosis

<400> SEQUENCE: 87

Ala Ile Gly Val Ala Thr Gly Ile Val Gln Glu Phe Gln Phe Gly Met
1 5 10 15

Asn

<210> SEQ ID NO: 88
<211> LENGTH: 17
<212> TYPE: PRT
<213> ORGANISM: Mycobacterium tuberculosis

<400> SEQUENCE: 88

-continued

Thr Gly Ile Val Gln Glu Phe Glu Phe Gly Met Asn Trp Ser Glu Tyr
1 5 10 15

Ser

<210> SEQ ID NO: 89
<211> LENGTH: 17
<212> TYPE: PRT
<213> ORGANISM: Mycobacterium tuberculosis

<400> SEQUENCE: 89

Glu Phe Gln Phe Gly Met Asn Trp Ser Glu Tyr Ser Arg Phe Val Gly
1 5 10 15

Asp

<210> SEQ ID NO: 90
<211> LENGTH: 17
<212> TYPE: PRT
<213> ORGANISM: Mycobacterium tuberculosis

<400> SEQUENCE: 90

Met Asn Trp Ser Glu Tyr Ser Arg Phe Val Gly Asp Val Phe Gly Ala
1 5 10 15

Pro

<210> SEQ ID NO: 91
<211> LENGTH: 17
<212> TYPE: PRT
<213> ORGANISM: Mycobacterium tuberculosis

<400> SEQUENCE: 91

Trp Ser Glu Tyr Ser Arg Phe Val Gly Asp Val Phe Gly Ala Pro Leu
1 5 10 15

Ala

<210> SEQ ID NO: 92
<211> LENGTH: 17
<212> TYPE: PRT
<213> ORGANISM: Mycobacterium tuberculosis

<400> SEQUENCE: 92

Glu Tyr Ser Arg Phe Val Gly Asp Val Phe Gly Ala Pro Leu Ala Met
1 5 10 15

Glu

<210> SEQ ID NO: 93
<211> LENGTH: 17
<212> TYPE: PRT
<213> ORGANISM: Mycobacterium tuberculosis

<400> SEQUENCE: 93

Ser Arg Phe Val Gly Asp Val Phe Gly Ala Pro Leu Ala Met Glu Ser
1 5 10 15

Leu

<210> SEQ ID NO: 94
<211> LENGTH: 17
<212> TYPE: PRT
<213> ORGANISM: Mycobacterium tuberculosis

<400> SEQUENCE: 94

-continued

Trp Ile Phe Gly Trp Asn Arg Leu Pro Arg Leu Val His Leu Ala Cys
1 5 10 15

Ile

<210> SEQ ID NO: 95
<211> LENGTH: 17
<212> TYPE: PRT
<213> ORGANISM: Mycobacterium tuberculosis

<400> SEQUENCE: 95

Trp Asn Arg Leu Pro Arg Leu Val His Leu Ala Cys Ile Trp Ile Val
1 5 10 15

Ala

<210> SEQ ID NO: 96
<211> LENGTH: 17
<212> TYPE: PRT
<213> ORGANISM: Mycobacterium tuberculosis

<400> SEQUENCE: 96

Gly Arg Ala Glu Leu Ser Ser Ile Val Val Leu Leu Thr Asn Asn Thr
1 5 10 15

Ala

<210> SEQ ID NO: 97
<211> LENGTH: 17
<212> TYPE: PRT
<213> ORGANISM: Mycobacterium tuberculosis

<400> SEQUENCE: 97

Gly Lys Thr Tyr Asp Ala Tyr Phe Thr Asp Ala Gly Gly Ile Thr Pro
1 5 10 15

Gly

<210> SEQ ID NO: 98
<211> LENGTH: 17
<212> TYPE: PRT
<213> ORGANISM: Mycobacterium tuberculosis

<400> SEQUENCE: 98

Tyr Asp Ala Tyr Phe Thr Asp Ala Gly Gly Ile Thr Pro Gly Asn Ser
1 5 10 15

Val

<210> SEQ ID NO: 99
<211> LENGTH: 17
<212> TYPE: PRT
<213> ORGANISM: Mycobacterium tuberculosis

<400> SEQUENCE: 99

Trp Pro Gln Gly Lys Thr Tyr Asp Ala Tyr Phe Thr Asp Ala Gly Gly
1 5 10 15

Ile

<210> SEQ ID NO: 100
<211> LENGTH: 17
<212> TYPE: PRT
<213> ORGANISM: Mycobacterium tuberculosis

<400> SEQUENCE: 100

Ala Thr Gly Met Ala Glu Thr Val Ala Ser Phe Ser Pro Ser Glu Gly

-continued

```
 1               5                  10                  15

Ser


<210> SEQ ID NO: 101
<211> LENGTH: 17
<212> TYPE: PRT
<213> ORGANISM: Mycobacterium tuberculosis

<400> SEQUENCE: 101

Gly Trp Glu Arg Arg Leu Arg His Ala Val Ser Pro Lys Asp Pro Ala
 1               5                  10                  15

Gln


<210> SEQ ID NO: 102
<211> LENGTH: 17
<212> TYPE: PRT
<213> ORGANISM: Mycobacterium tuberculosis

<400> SEQUENCE: 102

Thr Gly Ser Gly Glu Thr Thr Thr Ala Ala Gly Thr Thr Ala Ser Pro
 1               5                  10                  15

Gly


<210> SEQ ID NO: 103
<211> LENGTH: 17
<212> TYPE: PRT
<213> ORGANISM: Mycobacterium tuberculosis

<400> SEQUENCE: 103

Gly Ala Ala Ile Leu Val Ala Gly Leu Ser Gly Cys Ser Ser Asn Lys
 1               5                  10                  15

Ser


<210> SEQ ID NO: 104
<211> LENGTH: 17
<212> TYPE: PRT
<213> ORGANISM: Mycobacterium tuberculosis

<400> SEQUENCE: 104

Ala Val Ala Gly Ala Ala Ile Leu Val Ala Gly Leu Ser Gly Cys Ser
 1               5                  10                  15

Ser


<210> SEQ ID NO: 105
<211> LENGTH: 17
<212> TYPE: PRT
<213> ORGANISM: Mycobacterium tuberculosis

<400> SEQUENCE: 105

Leu Thr Val Ala Val Ala Gly Ala Ala Ile Leu Val Ala Gly Leu Ser
 1               5                  10                  15

Gly


<210> SEQ ID NO: 106
<211> LENGTH: 21
<212> TYPE: DNA
<213> ORGANISM: Mycobacterium tuberculosis
<220> FEATURE:
<223> OTHER INFORMATION: Description of Artificial Sequence:PCR Primer

<400> SEQUENCE: 106
```

-continued cccagcttgt gatacaggag g 21

<210> SEQ ID NO: 107
<211> LENGTH: 22
<212> TYPE: DNA
<213> ORGANISM: Mycobacterium tuberculosis
<220> FEATURE:
<223> OTHER INFORMATION: Description of Artificial Sequence:PCR Primer

<400> SEQUENCE: 107
ggcctcagcg cggctccgga gg 22

<210> SEQ ID NO: 108
<211> LENGTH: 46
<212> TYPE: DNA
<213> ORGANISM: Mycobacterium tuberculosis
<220> FEATURE:
<223> OTHER INFORMATION: Description of Artificial Sequence:PCR Primer

<400> SEQUENCE: 108
tctagacacc accaccacca ccacgtgaca cctcgcgggc caggtc 46

<210> SEQ ID NO: 109
<211> LENGTH: 28
<212> TYPE: DNA
<213> ORGANISM: Mycobacterium tuberculosis
<220> FEATURE:
<223> OTHER INFORMATION: Description of Artificial Sequence:PCR Primer

<400> SEQUENCE: 109
aagcttcgcc atgccgccgg taagcgcc 28

<210> SEQ ID NO: 110
<211> LENGTH: 330
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 110
gcacgtcgtc gccagtgcca accagggccc ggggcnnacc agctcgccga tccacggcaa 60
caacgagacg tagaacacca ggccgaatag caggccgtag cccagcccac ccaccggtgt 120
cgtcgcgcgg tgggtcagca cccaggccag caatgcgnag cccaaccacc gccgnccacc 180
agcagttgcg cggcgggaag ctggcataca acagcagacc ggccacgatg ctgaccacca 240
ggcgcgtcan ccgcgtccgc accgngtccc gtgtggtggg cagctgcgct ncacccakkc 300
kccaagcttc accanggcgc cgscgggccg 330

<210> SEQ ID NO: 111
<211> LENGTH: 431
<212> TYPE: DNA
<213> ORGANISM: Mycobacterium tuberculosis
<220> FEATURE:
<221> NAME/KEY: Modified base
<223> OTHER INFORMATION: n represents a or g or c or t/u

<400> SEQUENCE: 111
tgtcccgcat ggtagtcggg ctggnccngg tgatcgcttg cagctttngc cgtggatgtg 60
agaaaggaat atgttggtga tcaccatgtt tcgtgtactc gtggcgcgga tgacggcgct 120
ggcggtcgac gangtcgggc atgtccaccg tggaatacgc catcggtacc atcgcggcgg 180
ctgcnttcgg tgcgatcctc tacacggtcg tcaccgggga ttccattgtg tcggcgctca 240

-continued accgcatcat cggtcgcgcg ctcagcacca aggtttagcg tcgtgtgcgg gtgcgagcac 300
cgtggaagcg gcgttggcga tcgccaccct ggtgctggtg ctggtgctgt gcctggcggg 360
cgtcaccgcg gtatcaatgc aggtgcgctg tatcgacgcg gcccgcgagg ccgctcgatt 420
ggccgcgcgc g 431

<210> SEQ ID NO: 112
<211> LENGTH: 143
<212> TYPE: PRT
<213> ORGANISM: Mycobacterium tuberculosis

<400> SEQUENCE: 112

Ala Gly Gly Cys Gly Ala Cys Gly Gly Thr Thr Gly Gly Cys Ala Cys
1 5 10 15

Cys Ala Cys Cys Ala Cys Gly Ala Gly Thr Gly Ala Gly Thr Cys Ala
20 25 30

Gly Gly Cys Ala Gly Gly Ala Gly Cys Cys Cys Cys Gly Cys Cys Ala
35 40 45

Cys Gly Thr Thr Gly Cys Gly Gly Ala Cys Gly Gly Cys Gly Cys Gly
50 55 60

Ala Ala Thr Cys Thr Thr Cys Gly Cys Cys Thr Gly Thr Gly Gly Cys
65 70 75 80

Thr Cys Ala Cys Cys Gly Ala Cys Thr Thr Thr Cys Cys Gly Cys Cys
85 90 95

Cys Ala Ala Cys Thr Thr Cys Ala Ala Cys Gly Ala Thr Cys Thr Thr
100 105 110

Gly Cys Ala Cys Ala Thr Gly Gly Ala Cys Gly Gly Cys Ala Ala Gly
115 120 125

Ala Ala Cys Gly Cys Cys Gly Ala Gly Gly Thr Cys Gly Cys Gly
130 135 140

<210> SEQ ID NO: 113
<211> LENGTH: 363
<212> TYPE: PRT
<213> ORGANISM: Mycobacterium tuberculosis

<400> SEQUENCE: 113

Met Thr Pro Arg Gly Pro Gly Arg Leu Gln Arg Leu Ser Gln Cys Arg
1 5 10 15

Pro Gln Arg Gly Ser Gly Gly Pro Ala Arg Gly Leu Arg Gln Leu Ala
20 25 30

Leu Ala Ala Met Leu Gly Ala Leu Ala Val Thr Val Ser Gly Cys Ser
35 40 45

Trp Ser Glu Ala Leu Gly Ile Gly Trp Pro Glu Gly Ile Thr Pro Glu
50 55 60

Ala His Leu Asn Arg Glu Leu Trp Ile Gly Ala Val Ile Ala Ser Leu
65 70 75 80

Ala Val Gly Val Ile Val Trp Gly Leu Ile Phe Trp Ser Ala Val Phe
85 90 95

His Arg Lys Lys Asn Thr Asp Thr Glu Leu Pro Arg Gln Phe Gly Tyr
100 105 110

Asn Met Pro Leu Glu Leu Val Leu Thr Val Ile Pro Phe Leu Ile Ile
115 120 125

Ser Val Leu Phe Tyr Phe Thr Val Val Val Gln Glu Lys Met Leu Gln
130 135 140

-continued

```
Ile Ala Lys Asp Pro Glu Val Val Ile Asp Ile Thr Ser Phe Gln Trp
145                 150                 155                 160

Asn Trp Lys Phe Gly Tyr Gln Arg Val Asn Phe Lys Asp Gly Thr Leu
                165                 170                 175

Thr Tyr Asp Gly Ala Asp Pro Glu Arg Lys Arg Ala Met Val Ser Lys
            180                 185                 190

Pro Glu Gly Lys Asp Lys Tyr Gly Glu Glu Leu Val Gly Pro Val Arg
        195                 200                 205

Gly Leu Asn Thr Glu Asp Arg Thr Tyr Leu Asn Phe Asp Lys Val Glu
    210                 215                 220

Thr Leu Gly Thr Ser Thr Glu Ile Pro Val Leu Val Leu Pro Ser Gly
225                 230                 235                 240

Lys Arg Ile Glu Phe Gln Met Ala Ser Ala Asp Val Ile His Ala Phe
                245                 250                 255

Trp Val Pro Glu Phe Leu Phe Lys Arg Asp Val Met Pro Asn Pro Val
            260                 265                 270

Ala Asn Asn Ser Val Asn Val Phe Gln Ile Glu Glu Ile Thr Lys Thr
        275                 280                 285

Gly Ala Phe Val Gly His Cys Ala Glu Met Cys Gly Thr Tyr His Ser
    290                 295                 300

Met Met Asn Phe Glu Val Arg Val Val Thr Pro Asn Asp Phe Lys Ala
305                 310                 315                 320

Tyr Leu Gln Gln Arg Ile Asp Gly Asn Thr Asn Ala Glu Ala Leu Arg
                325                 330                 335

Ala Ile Asn Gln Pro Pro Leu Ala Val Thr Thr His Pro Phe Asp Thr
            340                 345                 350

Arg Arg Gly Glu Leu Ala Pro Gln Pro Val Gly
        355                 360
```

*MYCOBACTERIUM TUBERCULOSIS* DNA SEQUENCES ENCODING IMMUNOSTIMULATORY PEPTIDES

CROSS REFERENCE TO RELATED CASES

This application is a continuation in part of co-pending PCT application U.S. 96/10375, filed Jun. 14, 1996, and claims the benefit of U.S. Provisional Application No. 60/000,254, filed Jun. 15, 1995, which applications are incorporated herein by reference.

I. BACKGROUND

A. The Rise of Tuberculosis

Over the past few years the editors of the Morbidity and Mortality Weekly Report have chronicled the unexpected rise in tuberculosis cases. It has been estimated that worldwide there are one billion people infected with *M. tuberculosis,* with 7.5 million active cases of tuberculosis. Even in the United States, tuberculosis continues to be a major problem especially among the homeless, Native Americans, African-Americans, immigrants, and the elderly. HIV-infected individuals represent the newest group to be affected by tuberculosis. Of the 88 million new cases of tuberculosis expected in this decade approximately 10% will be attributable to HIV infection.

The emergence of multi-dug resistant strains of *M. tuberculosis* has complicated matters further and even raises the possibility of a new tuberculosis epidemic. In the U.S. about 14% of *M. tuberculosis* isolates are resistant to at least one drug, and approximately 3% are resistant to at least two drugs. *M. tuberculosis* strains have even been isolated that are resistant to all seven drugs in the repertoire of drugs commonly used to combat tuberculosis. Resistant strains make treatment of tuberculosis extremely difficult: for example, infection with *M. tuberculosis* strains resistant to isoniazid and rifampin leads to mortality rates of approximately 90% among HIV-infected individuals. The mean time to death after diagnosis in this population is 4–16 weeks. One study reported that of nine immunocompetent health care workers and prison guards infected with drug resistant *M. tuberculosis,* five died. The expected mortality rate for infection with drug sensitive *M. tuberculosis* is 0%.

The unrelenting persistence of mycobacterial disease worldwide, the emergence of a new, highly susceptible population, and the recent appearance of drug resistant strains point to the need for new and better prophylactic and therapeutic treatments of mycobacterial diseases.

B. Tuberculosis and the Immune System

Infection with *M. tuberculosis* can take on many manifestations. The growth in the body of *M. tuberculosis* and the pathology that it induces is largely dependent on the type and vigor of the immune response. From mouse genetic studies it is known that innate properties of the macrophage play a large role in containing disease (1). Initial control of *M. tuberculosis* may also be influenced by reactive γδ T cells. However, the major immune response responsible for containment of *M. tuberculosis* is via helper T cells (Th1) and to a lesser extent cytotoxic T cells (2). Evidence suggests that there is very little role for the humoral response. The ratio of responding Th1 to Th2 cells has been proposed to be involved in the phenomenon of suppression.

Th1 cells are thought to convey protection by responding to *M. tuberculosis* T cell epitopes and secreting cytokines, particularly interferon-γ, which stimulate macrophages to kill *M. tuberculosis.* While such an immune response normally clears infections by many facultative intracellular pathogens, such as Salmonella, Listeria or Francisella, it is only able to contain the growth of other pathogens such as *M. tuberculosis* and Toxoplasma. Hence, it is likely that *M. tuberculosis* has the ability to suppress a clearing immune response, and mycobacterial components such as lipoarabinomannan are thought to be potential agents of this suppression. Dormant *M. tuberculosis* can remain in the body for long periods of time and can emerge to cause disease when the immune system wanes due to age or other effects such as infection with HIV-1.

Historically it has been thought that one needs replicating Mycobacteria in order to effect a protective immunization. An hypothesis explaining the molecular basis for the effectiveness of replicating mycobacteria in inducing protective immunity has been proposed by Orme and co-workers (3). These scientists suggest that antigens are pinocytosed from the mycobacteria-laden phagosome and used in antigen presentation. This hypothesis also explains the basis for secreted proteins effecting a protective immune response.

Antigens that stimulate T cells from *M. tuberculosis* infected mice or from PPD-positive humans are found in both the whole mycobacterial cells and also in the culture supernatants (3, 4, 5–7, 34). Recently Pal and Horwitz (8) were able to induce partial protection in guinea pigs by vaccinating with *M. tuberculosis* supernatant fluids. Similar results were found by Andersen using a murine model of tuberculosis (9). Other studies include reference nos. 34, 12. Although these works are far from definitive they do strengthen the notion that protective epitopes can be found among secreted proteins and that a non-living vaccine can protect against tuberculosis.

For the purposes of vaccine development one needs to find epitopes that confer protection but do not contribute to pathology. An ideal vaccine would contain a cocktail of T-cell epitopes that preferentially stimulate Th1 cells and are bound by different MHC haplotypes. Although such vaccines have never been made there is at least one example of a synthetic T-cell epitope inducing protection against an intracellular pathogen (10). It is an object of this invention to provide *M. tuberculosis* DNA sequences that encode bacterial peptides having an immunostimulatory activity. Such immunostimulatory peptides will be useful in the treatment, diagnosis and prevention of tuberculosis.

II. SUMMARY OF THE INVENTION

The present invention provides DNA sequences isolated from *Mycobacterium tuberculosis.* Peptides encoded by these DNA sequences are shown to stimulate the production of the macrophage-stimulating cytokine, gamma interferon ("INF-γ"), in mice. Critically, the production of INF-γ by CD4 cells in mice has been shown to correlate with maximum expression of protective immunity against tuberculosis (11). Furthermore, in human patients with active "minimal" or "contained" tuberculosis, it appears that the containment of the disease may be attributable, at least in part, to the production of CD4 Th-1-like lymphocytes that release INF-γ (12).

Hence, the DNA sequences provided by this invention encode peptides that are capable of stimulating T-cells to produce INF-γ. That is, these peptides act as epitopes for CD4 T-cells in the immune system. Studies have demonstrated that peptides isolated from an infectious agent and which are shown to be T-cell epitopes can protect against the disease caused by that agent when administered as a vaccine (13, 10). For example, T-cell epitopes from the parasite

*Leishmania major* have been shown to be effective when administered as a vaccine (10, 13–14). Therefore, the immunostimulatory peptides (T-cell epitopes) encoded by the disclosed DNA sequences may be used, in purified form, as a vaccine against tuberculosis.

As noted, the nucleotide sequences of the present invention encode immunostimulatory peptides. In a number of instances, these nucleotide sequences are only a part of a larger open reading frame (ORF) of an *M. tuberculosis* operon. The present invention enables the cloning of the complete ORF using standard molecular biology techniques, based on the nucleotide sequences provided herein. Thus, the present invention encompasses both the nucleotide sequences disclosed herein and the complete *M. tuberculosis* ORFs to which they correspond. However, it is noted that since each of the nucleotide sequences disclosed herein encodes an immunostimulatory peptide, the use of larger peptides encoded by the complete ORFs is not necessary for the practice of the invention. Indeed, it is anticipated that, in some instances, proteins encoded by the corresponding ORFs may be less immunostimulatory than the peptides encoded by the nucleotide sequences provided herein.

One aspect of the present invention is an immunostimulatory preparation comprising at least one peptide encoded by the DNA sequences presented herein. Such a preparation may include the purified peptide or peptides and one or more pharmaceutically acceptable adjuvants, diluents and/or excipients. Another aspect of the invention is a vaccine comprising one or more peptides encoded by nucleotide sequences provided herein. This vaccine may also include one or more pharmaceutically acceptable excipients, adjuvants and/or diluents.

Another aspect of the present invention is an antibody specific for an immunostimulatory peptide encoded by a nucleotide sequence of the present invention. Such antibodies may be used to detect the present of *M. tuberculosis* antigens in medical specimens, such as blood or sputum. Thus, these antigens may be used to diagnose tuberculosis infections.

The present invention also encompasses the diagnostic use of purified peptides encoded by the nucleotide sequences of the present invention. Thus, the peptides may be used in a diagnostic assay to detect the presence of antibodies in a medical specimen, which antibodies bind to the *M. tuberculosis* peptide and indicate that the subject from which the specimen was removed was previously exposed to *M. tuberculosis.*

The present invention also provides an improved method of performing the tuberculin skin test to diagnose exposure of an individual to *M. tuberculosis.* In this improved skin test, purified immunostimulatory peptides encoded by the nucleotide sequences of this invention are employed. Preferably, this skin test is performed with one set of the immunostimulatory peptides, while another set of the immunostimulatory peptides is used to formulate vaccine preparations. In this way, the tuberculin skin test will be useful in distinguishing between subjects infected with tuberculosis and subjects who have simply been vaccinated. In this manner, the present invention may overcome a serious limitation inherent in the present BCG vaccine/tuberculin skin test combination.

Other aspects of the present invention include the use of probes and primers derived from the nucleotide sequences disclosed herein to detect the presence of *M. tuberculosis* nucleic acids in medical specimens.

A further aspect of the present invention is the discovery that a significant proportion of the immunostimulatory peptides are homologous to proteins known to be located in bacterial cell surface membranes. This discovery suggests that membrane-bound peptides, particularly those from *M. tuberculosis,* may be a new source of antigens for use in vaccine preparations.

III. BRIEF DESCRIPTION OF THE DRAWINGS

FIG. 1 shows the deduced amino acid sequence of the full length MTB2-92 protein. The nucleic acid sequence is contained within Seq. I.D. No. 67, the amino acid sequence is shown in Seq. I.D. No. 113.

IV. DESCRIPTION OF THE INVENTION

A. Definitions

Particular terms and phrases used herein have the meanings set forth below.

"Isolated". An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

The nucleic acids of the present invention comprise at least a minimum length able to hybridize specifically with a target nucleic acid (or a sequence complementary thereto) under stringent conditions as defined below. The length of a nucleic acid of the present invention is preferably 15 nucleotides or greater in length, although a shorter nucleic acid may be employed as a probe or primer if it is shown to specifically hybridize under stringent conditions with a target nucleic acid by methods well known in the art. The phrase a "peptide of the present invention" means a peptide encoded by a nucleic acid molecule as defined in this paragraph.

"Probes" and "primers". Nucleic acid probes and primers may readily be prepared based on the nucleic acid sequences provided by this invention. A "probe" comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in reference nos. 15 and 16.

"Primers" are short nucleic acids, preferably DNA oligonucleotides 15 nucleotides or more in length, which are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

As noted, probes and primers are preferably 15 nucleotides or more in length, but, to enhance specificity, probes and primers of 20 or more nucleotides may be preferred.

Methods for preparing and using probes and primers are described, for example, in reference nos. 15, 16 and 17. PCR primer pairs can be derived from a known sequence, for example, by using computer programs intended for that purpose such as Primer (Version 0.5, © 1991, Whitehead Institute for Biomedical Research, Cambridge, Mass.).

"Substantial similarity". A first nucleic acid is "substantially similar" to a second nucleic acid if, when optimally aligned (with appropriate nucleotide insertions or deletions) with the other nucleic acid (or its complementary strand), there is nucleotide sequence identity in at least about 75%–90% of the nucleotide bases, and preferably greater than 90% of the nucleotide bases. ("Substantial sequence complementarity" requires a similar degree of sequence complementarity.) Sequence similarity can be determined by comparing the nucleotide sequences of two nucleic acids using sequence analysis software such as the Sequence Analysis Software Package of the Genetics Computer Group, University of Wisconsin Biotechnology Center, Madison, Wis.).

"Operably linked". A first nucleic acid sequence is "operably" linked with a second nucleic acid sequence when the first nucleic acid sequence is placed in a functional relationship with the nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Recombinant". A "recombinant" nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

"Stringent Conditions" and "Specific". The nucleic acid probes and primers of the present invention hybridize under stringent conditions to a target DNA sequence, e.g., to a full length *Mycobacterium tuberculosis* gene that encodes an immunostimulatory peptide.

The term "stringent conditions" is functionally defined with regard to the hybridization of a nucleic-acid probe to a target nucleic acid (i.e., to a particular nucleic acid sequence of interest) by the hybridization procedure discussed in Sambrook et al. (1989) (reference no. 15) at 9.52–9.55. See also, reference no. 15 at 9.47–9.52, 9.56–9.58; reference no. 18 and reference no. 19.

Nucleic-acid hybridization is affected by such conditions as salt concentration, temperature, or organic solvents, in addition to the base composition, length of the complementary strands, and the number of nucleotide-base mismatches between the hybridizing nucleic acids, as will be readily appreciated by those skilled in the art.

In preferred embodiments of the present invention, stringent conditions are those under which DNA molecules with more than 25% sequence variation (also termed "mismatch") will not hybridize. Such conditions are also referred to as conditions of 75 % stringency (since hybridization will occur only between molecules with 75% sequence identity or greater). In more preferred embodiments, stringent conditions are those under which DNA molecules with more than 15% mismatch will not hybridize (conditions of 85% stringency). In most preferred embodiments, stringent conditions are those under which DNA molecules with more that 10% mismatch will not hybridize (i.e. conditions of 90% stringency).

When referring to a probe or primer, the term "specific for (a target sequence)" indicates that the probe or primer hybridizes under stringent conditions substantially only to the target sequence in a given sample comprising the target sequence.

"Purified"—a "purified" peptide is a peptide that has been extracted from the cellular environment and separated from substantially all other cellular peptides. As used herein, the term peptide includes peptides, polypeptides and proteins. In preferred embodiments, a "purified" peptide is a preparation in which the subject peptide comprises 80% or more of the protein content of the preparation. For certain uses, such as vaccine preparations, even greater purity may be necessary.

"Immunostimulatory"—the phrase "immunostimulatory peptide" as used herein refers to a peptide that is capable of stimulating INF-γ production in the assay described in section B 5 below. In preferred embodiments, an immunostimulatory peptide is one capable of inducing greater than twice the background level of this assay determined using T-cells stimulated with no antigens or negative control antigens. Preferably, the immunostimulatory peptides are capable of inducing more than 0.01 ng/ml of INF-γ in this assay system. In more preferred embodiments, an immunostimulatory peptide is one capable of inducing greater than 10 ng/ml of INF-γ in this assay system.

B. Materials and Methods

1. Standard Methodologies

The present invention utilizes standard laboratory practices for the cloning, manipulation and sequencing of nucleic acids, purification and analysis of proteins and other molecular biological and biochemical techniques, unless otherwise stipulated. Such techniques are explained in detail in standard laboratory manuals such as Sambrook et al. (15); and Ausubel et al. (16).

Methods for chemical synthesis of nucleic acids are discussed, for example, in reference nos. 20 and 21. Chemical synthesis of nucleic acids can be performed, for example, on commercial automated oligonucleotide synthesizers.

2. Isolation of *Mycobacterium Tuberculosis* DNA Sequences Encoding Immunostimulatory Proteins

*Mycobacterium tuberculosis* DNA was obtained by the method of Jacobs et al. (22). Samples of the isolated DNA were partially digested with one of the following restriction enzymes HinPI, HpaII, AciI, TaqI, BsaHI, NarI. Digested fragments of 0.2–5 kb were purified from agarose gels and then ligated into the BstBI site in front of the truncated phoA gene in one or more of the three phagemid vectors pJDT1, pJDT2, and JDT3.

A schematic representation of the phagemid vector pJDT2 is provided in Mdluli et al. (1995) (reference no. 31). The pJDT vectors were specifically designed for cloning and selecting genes encoding cell wall-associated, cytoplasmic membrane associated, periplasmic or secreted proteins (and especially for cloning such genes from GC rich genomes, such as the *Mycobacterium tuberculosis* genome). The vectors have a BstBI cloning site in frame with the bacterial alkaline phosphatase gene (phoA) such that cloning of an in-frame sequence into the cloning site will result in the production of a fusion protein. The phoA gene encodes a version of the alkaline phosphatase that lacks a signal sequence; hence, only if the DNA cloned into the BstBI site includes a signal sequence or a transmembrane sequence can the fusion protein be secreted to the medium or inserted into cytoplasmic membrane, periplasm or cell wall. Those clones encoding such fusion proteins may be detected by plating clones on agar plates containing the indicator 5-bromo-4-chloro-3-indolyl-phosphate. Alkaline phosphatase converts this indicator to a blue colored product. Hence, those clones containing secreted alkaline phosphatase fusion proteins will produce the blue color.

The three vectors in this series (pJDT1, 2 and 3) have the BstBI restriction sites located in different reading frames with respect to the phoA gene. This increases the likelihood of cloning any particular gene in the correct orientation and reading frame for expression by a factor of 3. Reference no. 31 describes pJDT vectors in detail.

3. Selection of Secreted Fusion Proteins

The recombinant clones described above were transformed into *E. coli* and plated on agar plates containing the indicator 5-bromo-4-chloro-3-indolyl-phosphate. Production of blue pigmentation, produced as a result of the action of alkaline phosphatase on the indicator, indicated the presence of secreted cytoplasmic membrane periplasmic, cell wall associated or outer membrane fusion proteins (because the bacterial alkaline phosphatase gene in the vector lacks a signal sequence and could not otherwise escape the bacterial cell). A similar technique has been used to identify *M. tuberculosis* genes encoding exported proteins by Lim et al. (32).

Those clones producing blue pigmentation were picked and grown in liquid culture to facilitate the purification of the alkaline phosphatase fusion proteins. These recombinant clones were designated according to the restriction enzyme used to digest the *Mycobacterium tuberculosis* DNA (thus, clones designated A#2-1, A#2-2 etc were produced using *Mycobacterium tuberculosis* DNA digested with AciI).

4. Purification of Secreted Fusion Proteins

PhoA fusion proteins were extracted from the selected *E. coli* clones by cell lysis and purified by SDS polyacrylamide gel electrophoresis. Essentially, individual *E. coli* clones are grown overnight at 30° C. with shaking in 2 ml LB broth containing ampicillin, kanamycin and IPTG. The cells are precipitated by centrifugation and resuspended in 100 μL Tris -EDTA buffer. 100 μL lysis buffer (1% SDS, 1 mMEDTA, 25 mM DTT, 10% glycerol and 50 mM tris-HCl, pH 7.5) is added to this mixture and DNA released from the cells is sheared by passing the mixture through a small gauge syringe needle. The sample is then heated for 5 minutes at 100° C. and loaded onto an SDS PAGE gel (12 cm×14 cm×1.5 mm, made with 4% (w/v) acrylamide in the stacking section and 10% (w/v) acrylamide in the separating section). Several samples from each clone are loaded onto each gel.

The samples are electrophoresed by application of 200 volts to the gel for 4 hours. Subsequently, the proteins are transferred to a nitrocellulose membrane by Western blotting. A strip of nitrocellulose is cut off to be processed with antibody, and the remainder of the nitrocellulose is set aside for eventual elution of the protein. The strip is incubated with blocking buffer and then with anti-alkaline phosphatase primary antibody, followed by incubation with anti-mouse antibody conjugated with horse radish peroxidase. Finally, the strip is developed with the NEN DuPont Renaissance kit to generate a luminescent signal. The migratory position of the PhoA fusion protein, as indicated by the luminescent label, is measured with a ruler, and the corresponding region of the undeveloped nitrocellulose blot is excised.

This region of nitrocellulose, which contains the PhoA fusion protein, is then incubated in 1 ml 20% acetronitrile at 37° C. for 3 hours. Subsequently, the mixture is centrifuged to remove the nitrocellulose and the liquid is transferred to a new test tube and lyophilized. The resulting protein pellet is dissolved in 100 μL of endotoxin-free, sterile water and precipitated with acetone at −20° C. After centrifugation the bulk of the acetone is removed and the residual acetone is allowed to evaporate. The protein pellet is re-dissolved in 100 μL of sterile phosphate buffered saline. This procedure can be scaled up by modification to include IPTG induction 2 hours prior to cell harvesting, washing nitrocellulose membranes with PBS prior to acetonitrile extraction and lyophilization of acetonitrile extracted and acetone precipitated protein samples.

5. Determination of Immunostimulatory Capacity in Mice

The purified alkaline phosphatase—*Mycobacterium tuberculosis* fusion peptides encoded by the recombinant clones were then tested for their ability to stimulate INF-γ production in mice. The test used to determine INF-γ stimulation is as essentially that described by Orme et al. (11).

Essentially, the assay method is as follows: The virulent strain *M. tuberculosis* Erdman is grown in Proskauer Beck medium to mid-log phase, then aliquoted and frozen at −70° C. for use as an inoculant. Cultures of this bacterium are grown and harvested and nice are inoculated with $1\times10^5$ viable bacteria suspended in 200 μl sterile saline via a lateral tail vein on day one of the test.

Bone marrow-derived macrophages are used in the test to present the bacterial alkaline phosphatase-*Mycobacterium tuberculosis* fusion protein antigens. These macrophages are obtained by harvesting cells from mouse femurs and culturing the cells in Dulbecco's modified Eagle medium as described by Orme et al. (11). Eight to ten days later, up to ten μg of the fusion peptide to be tested is added to the macrophages and the cells are incubated for 24 hours.

The CD4 cells are obtained by harvesting spleen cells from the infected mice and then pooling and enriching for CD4 cells by removal of adherent cells by incubation on plastic Petri dishes, followed by incubation for 60 minutes at 37° C. with a mixture of J11d.2, Lyt-2.43, and GL4 monoclonal antibody (mAb) in the presence of rabbit complement to deplete B cells and immature T cells, CD8 cells, and γδ cells, respectively. The macrophages are overlaid with $10^6$ of these CD4 cells and the medium is supplemented with 5 U IL-2 to promote continued T cell proliferation and cytokine secretion. After 72 hours, cell supernatants are harvested from sets of triplicate wells and assayed for cytokine content.

Cytokine levels in harvested supernatants are assayed by sandwich ELISA as described by Orme et al. (11).

6. Determination of Immunostimulatory Capacity in Humans

The purified alkaline phosphatase—*Mycobacterium tuberculosis* fusion peptides encoded by the recombinant clones or by synthetic peptides are tested for their ability to induce INF-γ production by human T cells in the following manner.

Blood from tuberculin positive people (producing a tuberculin positive skin test) is collected in EDTA coated tubes, to prevent clotting. Mononuclear cells are isolated using a modified version of the separation procedure provided with the NycoPrep™ 1.077 solution (Nycomed Pharma AS, Oslo, Norway). Briefly, the blood is diluted in an equal volume of a physiologic solution, such as Hanks Balanced Salt solution (HBSS), and then gently layered over top of the Nycoprep solution in a 2 to 1 ratio in 50 ml tubes. The tubes are centrifuged at 800× g for 20 minutes and the mononuclear cells are then removed from the interface between the Nycoprep solution and the sample layer. The plasma is removed from the top of the tube and filtered through a 0.2 micron filter and is then added to the tissue culture media. The mononuclear cells are washed twice: the cells are diluted in a physiologic solution, such as HBSS or RPMI 1640, and centrifuged at 400× g for 10 minutes. The mononuclear cells are then resuspended to the desired concentration in tissue culture media (RPMI 1640 containing 10% autologous serum, Hepes, non-essential amino acids, antibiotics and polymixin B). The mononuclear cells are then cultured in 96 well microtitre plates.

Peptides or PhoA fusion proteins are then added to individual wells in the 96 well plate, and cells are then placed in an incubator (37° C., 5% $CO_2$). Samples of the supernatants (tissue culture media from the wells containing the cells) are collected at various time points (from 3 to 8 days) after the addition of the peptides or PhoA fusion proteins. The immune responsiveness of T cells to the peptides and PhoA fusion proteins is assessed by measuring the production of cytokines (including gamma-interferon).

Cytokines are measured using an Enzyme Linked Immunosorbent Assay (ELISA), the details of which are described in the Cytokine ELISA Protocol in the PharMingen catalogue (PharMingen, San Diego, Calif.). For measuring for the presence of human gamma-interferon, wells of a 96 well microtitre plate are coated with a capture antibody (anti-human gamma-interferon antibody). The sample supernatants are then added to individual wells. Any gamma-interferon present in the sample will bind to the capture antibody. The wells are then washed. A detection antibody (anti-human gamma-interferon antibody), conjugated to biotin, is added to each well, and will bind to any gamma-interferon that is bound to the capture antibody. Any unbound detection antibody is washed away. An avidin peroxidase enzyme is added to each well (avidin binds tightly to the biotin on the detection antibody). Any excess unbound enzyme is washed away. Finally, a chromogenic substrate for the enzyme is added and the intensity of the colour reaction that occurs is quantitated using an ELISA plate reader. The quantity of the gamma-interferon in the sample supernatants is determined by comparison with a standard curve using known quantities of human gamma-interferon.

Measurement of other cytokines, such as Interleukin-2 and Interleukin-4, can be determined using the same protocol, with the appropriate substitution of reagents (monoclonal antibodies and standards).

7. DNA Sequencing

The sequencing of the alkaline phosphatase fusion clones was undertaken using the AmpliCycle thermal sequencing kit (Perkin Elmer, Applied Biosystems Division, 850 Lincoln Centre Drive, Foster City, Calif. 94404, U.S.A.), using a primer designed to read out of the alkaline phosphatase gene into the *Mycobacterium tuberculosis* DNA insert, or primers specific to the cloned sequences.

C. Results

1. Immunostimulatory Capacity

More than 300 fusion clones were tested for their ability to stimulate INF-γ production. Of these, 80 clones were initially designated to have some ability to stimulate INF-γ production. Tables 1 and 2 show the data obtained for these 80 clones. Clones placed in Table 1 showed the greatest ability to stimulate INF-γ production (greater than 10 ng/ml of INF-γ) while clones placed in Table 2 stimulated the production of between 2 ng/ml and 10 ng/ml of INF-γ. Background levels of INF-γ production (i.e., levels produced without any added *M. tuberculosis* antigen) were subtracted from the levels produced by the fusions to obtain the figures shown in these tables.

TABLE 1

Immunostimulatory AP-fusion clones

| Seq ID | Name | INT | Sanger/TIGR ID of Mtb gene | Functional Identification |
|---|---|---|---|---|
| 2 | AciI#1-152 | >40,000 | MTCY16By.09 | glycerol-3-phosphate binding periplasmic protein precursor |
| 4 | AciI#1-247 | >40,000 | MTCI364.18 | fatty acid transport protein |
| 65,66 | AciI#1-264 | >40,000 | MTCY78.03c | unknown |
| 62 | AciI#1-435 | >40,000 | MTCY13D12.28 | EmbA |
| 75 | HinP#1-27 | >20,000 | unfin. TIGR/gmt 7458 | unknown |
| 67 | HinP#2-92 | >20,000 | MTCY190.11c | cytochrome c oxidase subunit II |
| 110 | HinP#2-145 | >20,000 | unfin. TIGR/gmt 7541 | unknown |
| 52 | HinP#2-150 | >20,000 | | |
| 48 | HinP#1-200 | >20,000 | unfin. TIGR/gmt 7491 | |
| 54 | HinP#3-30 | >20,000 | MTCY19H5.30c | |
| 6 | AciI#2-2 | >20,000 | MTV003.10c | lipoprotein, penicillin binding protein |
| 7 | AciI#2-23 | >20,000 | MTCY 13E10/unfin. TIGR/gmt 7508 | |
| 11 | AciI#2-506 | >20,000 | MTCY253.27c | γ-glutamyl transpeptidase precursor |
| 13 | AciI#2-511 | >20,000 | MTCY50.08c | unknown |
| 15 | AciI#2-639 | >20,000 | MTCY02B12.02 | unknown |
| 16 | AciI#2-822 | >20,000 | U27357 cds3/ unfin. TIGR gmt 7503 | unknown |
| 68 | AciI#2-823 | >20,000 | MTCY77.20 | unknown membrane protein |
| 61 | AciI#2-825 | >20,000 | MTCY31.03c | |
| 71 | AciI#2-827 | >20,000 | MTCY01B2.15c | cytochrome d (ubiquinol) oxidase (appC) |
| 22 | AciI#2-898 | >20,000 | unfin. TIGR/gmt 7554 | |
| 27 | AciI#2-1084 | >20,000 | unfin. TIGR/gmt 7458 | |
| 34 | AciI#3-47 | >20,000 | MTCY50.02 | oppA-like |
| 36 | AciI#3-133 | >20,000 | MTCY22G8 | complement of ORF designated |
| 38 | AciI#3-166 | >20,000 | MTCY20H10.03 (19H5) | unknown/contains potential membrane spanning region |
| 39 | AciI#3-167 | >20,000 | MTCI28.14 | unknown |
| 41 | AciI#3-206 | >20,000 | MTCY270.17 | ftsQ |
| 69 | HinP#1-31 | 14,638 | | 19kDa Antigen |
| 47 | HinP#1-144 | 13,546 | | unknown |
| 70 | HinP#1-3 | 11,550 | | |
| 111 | AciI#1-486 | 11,416 | MTCY13D12.26 | embC (LysR family) |
| 5 | AciI#1-426 | 11,135 | | |
| 23 | AciI#2-916 | 10,865 | MTCY21D4.03c | unknown (signal peptide) |

Abbreviations:
INF: pg/ml of INF-γ produced using fusion to stimulate immune T-cells.
Sanger/TGIR ID of *M. tuberculosis* gene: matches produced from BLAST search of TIGR and Sanger Center databases. For Sanger matches, the information prior to the decimal point (e.g., MTCY21D4) identifies the cosmid clone and the numbers after the decimal point (e.g., .03) indicate the matching ORF within that cosmid; "c" indicates that the clone matched with the complement of that cosmid ORF sequence.

TABLE 2

Immunostimulatory AP-fusion clones

| Seq ID | Clone Name | INT | Sanger/TIGR ID of Mtb gene | Functional Identification |
|---|---|---|---|---|
| 1 | AciI#1-62 | 3,126 | | |
| — | AciI#2-14 | 6,907 | | |
| 8 | AciI#2-26 | 3,089 | unfin. TIGR/gmt 7458 | unknown |
| 9 | AciI#2-35 | 3,907 | unfin. TIGR/gmt 7458 | unknown |
| 76 | AciI#2-147 | 5,464 | | |
| 12 | AciI#2-508 | 7,052 | MTCY20G9.23 | |
| — | AciI#2-510 | 2,445 | | |
| 14 | AciI#2-523 | 2,479 | MTCY427.10c | unknown |
| — | AciI#2-676 | 3,651 | | |
| 72 | AciI#2-834 | 5,942 | | |
| 17 | AciI#2-854 | 5,560 | MTCY339.08c | unknown |
| 18 | AciI#2-872 | 2,361 | MTCY22D7.18c | cstA-like |
| 73 | AciI#2-874 | 2,171 | MTCY190.20 | membrane protein |
| 19 | AciI#2-884D | 2,729 | | |
| 21 | AciI#2-894 | 3,396 | | unknown |
| 24 | AciI#2-1014 | 6,302 | | |
| 74 | AciI#2-1018 | 4,642 | MTCY270.11 | UDP-N-acetylmuramooylalanyl-D-glutamyl-2,6,diaminopimelate-D-alanyl-D-alanyl ligase (murF) |
| 25 | AciI#2-1025 | 3,582 | MTCY359.10 | unknown membrane protein |
| — | AciI#2-1034 | 2,736 | | |
| 26 | AciI#2-1035 | 3,454 | MTCY04D9.11c | similar to penicillin binding proteins |
| 28 | AciI#2-1089 | 8,974 | MTCY39.39 | mpt 64 |
| 29 | AciI#2-1090 | 7,449 | MTCY04C12.18c | unknown membrane protein |
| 30 | AciI#2-1104 | 5,148 | MTCY359.13 | Precursor of Apa wag43 locus |
| 31 | AciI#3-9 | 3,160 | MTCY164.01 | unknown |
| 32 | AciI#3-12 | 3,891 | | penicillin binding protein |
| 33 | AciI#3-15 | 4,019 | | |
| — | AciI#3-21 | 2,301 | | |
| 35 | AciI3-78 | 2,905 | | |
| 37 | AciI#3-134 | 3,895 | | |
| 40 | AciI#3-204 | 4,774 | | |
| 42 | AciI#3-214 | 7,333 | | unknown |
| 112 | AciI#3-243 | 2,857 | | |
| 43 | AciI#3-281 | 2,943 | MTCY19H5.32c | |
| 44 | Bsa HI#1-21 | 8,122 | | |
| 45 | HinP#1-12 | 2,905 | MTCY49.31c | unknown |
| 49 | HinP#2-23 | 2,339 | | |
| 46 | HinP#1-142 | 6,258 | MTCY02B10.27c | unknown |
| — | HinP#2-4 | 6,567 | | |
| 50 | HinP#2-143 | 3,689 | MTCY274,09c | unknown, thioredoxin-like |
| 51 | HinP#2-145A | 2,314 | | |
| — | HinP#2-147 | 7,021 | unfin. TIGR/gmt 7491 | |
| 53 | HinP#3-28 | 2,980 | | |
| 55 | HinP#3-34 | 2,564 | MTCY25D10.07 | unknown |
| 56 | HinP#3-41 | 3,296 | P31953 P31952 P17944 | Antigen 85c, 85b & 85a precursor |
| 57 | HpaII#1-3 | 2,360 | | |
| 58 | HpaII#1-8 | 2,048 | MTCY432 | unknown |
| 59 | HpaII#1-10 | 4,178 | | |
| 60 | HpaII#1-13 | 3,714 | MTCY16B7.47 | unknown partial ORF |

Abbreviations:
INF: pg/ml of INF-γ produced using fusion to stimulate immune T-cells: Sanger/TGIR ID of *M. tuberculosis* gene: matches prodcuced from BLAST search of TIGR and Sanger Center databases. For Sanger matches, the information prior to the decimal point (e.g., MTCY21D4) identifies the cosmid clone and the numbers after the decimal point (e.g., .03) indicate the matching ORF within that cosmid; "c" indicates that the clone matched with the complement of that cosmid ORF sequence.

2. DNA Sequencing and Determination of Open Reading Frames

DNA sequence data for the sequences of the *Mycobacterium tuberculosis* DNA present in the clones shown in Tables 1 and 2 are shown in the accompanying Sequence Listing. The sequences are believed to represent the coding strand of the Mycobacterium DNA. In most instances, these sequences represent only partial sequences of the immunostimulatory peptides and, in turn, only partial sequences of *Mycobacterium tuberculosis* genes. However, each of the clones from which these sequences were derived encodes, by itself, at least one immunostimulatory T-cell epitope. As discussed in part V below, one of ordinary skill in the art will, given the information provided herein, readily be able to obtain the immunostimulatory peptides and corresponding fill length *M. tuberculosis* genes using standard techniques. Accordingly, the nucleotide sequences of the present invention encompass not only those sequences presented in the sequence listings, but also the complete nucleotide sequence encoding the immunostimulatory peptides as well as the corresponding *M. tuberculosis* genes. The nucleotide abbreviations employed in the sequence listings are as follows in Table 3:

TABLE 3

| Symbol | Meaning |
|---|---|
| A | A; adenine |
| C | C; cytosine |
| G | G; guanine |
| T | T; thymine |
| U | U; uracil |
| M | A or C |
| R | A or G |
| W | A or T/U |
| S | C or G |
| Y | C or T/U |
| K | G or T/U |
| V | A or C or G; not T/U |
| H | A or C or T/U; not G |
| D | A or G or T/U; not C |
| B | C or G or T/U; not A |
| N | (A or C or G or T/U) or (unknown or other or no base) |
| — | indeterminate* |

*indicates an unreadable sequence compression.

The DNA sequences obtained were then analyzed with respect to the G+C content as a function of codon position over a window of 120 codons using the 'FRAME' computer program (Bibb, M. J.; Findlay, P. R.; and Johnson, M. W.; Gene 30: 157–166 (1984)). This program uses the bias of these nucleotides for each of the codon positions to enable the correct reading frame to be identified. As shown in tables 1 and 2, the sequences were also analyzed using the BLAST program on the TIGR database at the NCBI website (http://www.ncbi.gov/cgi-bin/BLAST/nph-tigrb1) and the Sanger Center website database (http://www/sanger.ac.uk/Projects/M_tuberculosis/blast_server.shtml). These sequence comparisons permitted matches with reported sequences to be identified and, for matches on the Sanger database, the identification of the open reading frame.

The sequence information revealed that a number of the clones contained overlapping sequence, as noted below:

| Clone | Overlapping clone(s) |
|---|---|
| HinP#1-27 | HinP#1-3 |
| HinP#2-92 | HinP#2-150, AciI#1-62, HpaII#1-3 |
| HinP#1-200 | AciI#2-147 |
| AciI#2-639 | AciI#2-676 |
| AciI#3-47 | AciI#3-204, AciI#3-243 |
| AciI#3-133 | AciI#3-134 |
| AciI#3-166 | AciI#3-15 |
| AciI#3-167 | AciI#3-78 |
| AciI#2-916 | AciI#2-1014 |
| AciI#2-1089 | HpaII#1-10 |
| AciI#3-243 | AciI#3-47 |

3. Identification of T Cell Epitopes in the Immunostimulatory Peptides

The T-Site program, by Feller, D. C. and de la Cruz, V. F., MedImmune Inc., 19 Firstfield Rd., Gaithersburg, Md. 20878, U.S.A., was used to predict T-cell epitopes from the determined coding sequences. It uses a series of four predictive algorithms. In particular, peptides were designed against regions indicated by the algorithm "A" motif which predicted alpha-helical periodicity (Margalit, H.; Spouge, J. L.; Cornette, J. L.; Cease, K. B.; DeLisi, C.; and Berzofsky, J. A., *J. Immunol.,* 138:2213 (1987)) and amphipathicity and those indicated by the algorithm "R" motif which identifies segments which display similarity to motifs known to be recognized by MHC class I and class II molecules (Rothbard, J. B. and Taylor, W. R., *EMBO J.* 7:93 (1988)). The other two algorithms identify classes of T-cell epitopes recognized in mice.

4. Synthesis of Synthetic Peptides Containing T Cell Epitopes in Identified Immunostimulatory Peptides A series of staggered peptides were designed to overlap regions indicated by the T-site analysis. These were synthesized by Chiron Mimotopes Pty. Ltd. (11055 Roselle St., San Diego, Calif. 92121, U.S.A.).

Peptides designed from sequences described in this application include:

| Peptide Sequence | Peptide Name | Seq I.D. No. |
|---|---|---|
| Hin P#1-200 (6 peptides) | | |
| VHLATGMAETVASFSPS | HPI1-200/2 | 77 |
| REVVHLATGMAETVASF | HPI1-200/3 | 78 |
| RDSREVVHLATGMAETV | HPI1-200/4 | 79 |
| DFNRDSREVVHLATGMA | HPI1-200/5 | 80 |
| ISAAVVTGYLRWTTPDR | HPI1-200/6 | 81 |
| AVVFLCAAAISAAVVTG | HPI1-200/7 | 82 |
| AciI#2-827 (14 peptides) | | |
| VTDNPAWYRLTKFFGKL | CD-2/1/96/1 | 83 |
| AWYRLTKFFGKLFLINF | CD-2/1/96/2 | 84 |
| KFFGKLFLINFAIGVAT | CD-2/1/96/3 | 85 |
| FLINFAIGVATGIVQEF | CD-2/1/96/4 | 86 |
| AIGVATGIVQEFQFGMN | CD-2/1/96/5 | 87 |
| TGIVQEFEFGMNWSEYS | CD-2/1/96/6 | 88 |
| EFQFGMNWSEYSRFVGD | CD-2/1/96/7 | 89 |
| MNWSEYSRFVGDVFGAP | CD-2/1/96/8 | 90 |
| WSEYSRFVGDVFGAPLA | CD-2/1/96/9 | 91 |
| EYSRFVGDVFGAPLAME | CD-2/1/96/10 | 92 |
| SRFVGDVFGAPLAMESL | CD-2/1/96/11 | 93 |
| WIFQWNRLPRLVHLACI | CD-2/1/96/12 | 94 |
| WNRLPRLVHLACIWIVA | CD-2/1/96/13 | 95 |
| GRAELSSIVVLLTNNTA | CD-2/1/96/14 | 96 |

-continued

| Peptide Sequence | Peptide Name | Seq I.D. No. |
|---|---|---|
| HinP#1-3 (2 peptides) | | |
| GKTYDAYFTDAGGITPG | HPI1-3/2 | 97 |
| YDAYFTDAGGITPGNSV | HPI1-3/3 | 98 |
| HinP#1-3/HinP#1-200 combined peptides | | |
| WPQGKTYDAYFTDAGGI (HinP#1-3) | HPI1-3/1 (combined) | 99 |
| ATGMAETVASFSPSEGS (HinP#1-200) | | 100 |
| AciI#2-823 (1 peptide) | | |
| GWERRLRHAVSPKDPAQ | AI2-823/1 | 101 |
| HinP#1-31 (4 peptides) | | |
| TGSGETTTAAGTTASPG | HPI1-31/1 | 102 |
| GAAILVAGLSGCSSNKS | HPI1-31/2 | 103 |
| AVAGAAILVAGLSGCSS | HPI1-31/3 | 104 |
| LTVAVAGAAILVAGLSG | HPI1-31/4 | 105 |

These synthetic peptides were resuspended in phosphate buffered saline to be tested to confirm their ability to function as T cell epitopes using the procedure described in part IV(B)(6) above.

5. Confirmation of Immunostimulatory Capacity using T Cells from Tuberculosis Patients The synthetic peptides described above, along with a number of the PhoA fusion proteins shown to be immunostimulatory in mice were tested for their ability to stimulate gamma interferon production in T-cells from tuberculin positive people using the methods described in part IV(B)(6) above. For each assay, $5\times10^5$ mononuclear cells were stimulated with up to 1 μg/ml *M. tuberculosis* peptide or up to 50 ng/ml Pho A fusion protein. *M. tuberculosis* filtrate proteins, Con A and PHA were employed as positive controls. An assay was run with media alone to determine background levels, and Pho A protein was employed as a negative control.

The results, shown in Table 4 below, indicate that all of the peptides tested stimulated gamma interferon production from T-cells of a particular subject.

TABLE 4

| Peptide or Pho A Fusion Protein Name | Concentration of Interferon-gamma (pg/ml) | Concentration of Interferon-gamma minus background (pg/ml) |
|---|---|---|
| CD-2/1/96/1 | 256.6 | 153.3 |
| CD-2/1/96/9 | 187.6 | 84.3 |
| CD-2/1/96/10 | 134.0 | 30.7 |
| CD-2/1/96/11 | 141.6 | 38.3 |
| CD-2/1/96/14 | 310.2 | 206.9 |
| HPI1-3/2 | 136.3 | 23.0 |
| HPI1-3/3 | 264.2 | 160.9 |
| AciI 2-898 | 134.0 | 30.7 |
| AciI 3-47 | 386.8 | 283.5 |
| *M. tuberculosis* filtrate proteins (10 μg/ml) | 256.6 | 153.3 |
| *M. tuberculosis* filtrate proteins (5 μg/ml) | 134.0 | 30.7 |
| Con A (10 μg/ml) | 2839 | 2735.7 |
| PHA (1%) | 10378 | 10274.7 |
| Pho A control (10 μg/ml) | 26.7 | 0 |
| Background | 103.3 | 0 |

V. CLONING OF FULL LENGTH *Mycobacterium Tuberculosis* T-Cell Epitope ORFs

Most the sequences presented represent only part of a larger *M. tuberculosis* ORF. If desired, the full length *M. tuberculosis* ORFs that include these provided nucleotide sequences can be readily obtained by one of ordinary skill in the art, based on the sequence data provided herein.

A. General Methodologies

Methods for obtaining full length genes based on partial sequence information are standard in the art and are particularly simple for prokaryotic genomes. By way of example, the full length ORFs corresponding to the DNA sequences presented herein may be obtained by creating a library of *Mycobacterium tuberculosis* DNA in a plasmid, bacteriophage or phagemid vector and screening this library with a hybridization probe using standard colony hybridization techniques. The hybridization probe consists of an oligonucleotide derived from a DNA sequence according to the present invention labelled with a suitable marker to enable detection of hybridizing clones. Suitable markers include radionuclides, such as P-32 and non-radioactive markers, such as biotin. Methods for constructing suitable libraries, production and labelling of oligonucleotide probes and colony hybridization are standard laboratory procedures and are described in standard laboratory manuals such as in reference nos. 15 and 16.

Having identified a clone that hybridizes with the oligonucleotide, the clone is identified and sequenced using standard methods such as described in Chapter 13 of reference no. 15. Determination of the translation initiation point of the DNA sequence enables the ORF to be located.

An alternative approach to cloning the full length ORFs corresponding to the DNA sequences provided herein is the use of the polymerase chain reaction (PCR). In particular, the inverse polymerase chain reaction (IPCR) is useful to isolate DNA sequences flanking a known sequence. Methods for amplification of flanking sequences by IPCR are described in Chapter 27 of reference no. 17 and in reference no. 23.

Accordingly, one aspect of the present invention is small oligonucleotides encompassed by the DNA sequences presented in the Sequence Listing. These small oligonucleotides are useful as hybridization probes and PCR primers that can be employed to clone the corresponding full length *Mycobacterium tuberculosis* ORFs. In preferred embodiments, these oligonucleotides will comprise at least 15 contiguous nucleotides of a DNA sequence set forth in the Sequence Listing, and in more preferred embodiments, such oligonucleotides will comprise at least 20 contiguous nucleotides of a DNA sequence set forth in the Sequence Listing.

One skilled in the art will appreciate that hybridization probes and PCR primers are not required to exactly match the target gene sequence to which they anneal. Therefore, in another embodiment, the oligonucleotides will comprise a sequence of at least 15 nucleotides and preferably at least 20 nucleotides, the oligonucleotide sequence being substantially similar to a DNA sequence set forth in the Sequence Listing. Preferably, such oligonucleotides will share at least about 75%–90% sequence identity with a DNA sequence set forth in the Sequence Listing and more preferably the shared sequence identity will be greater than 90%.

B. Example—Cloning of the Full Length ORF Corresponding to Clone HinP #2-92

Using the techniques described below, the full length gene corresponding to the clone HinP #2-92 was obtained. This gene, herein termed mtb2-92 includes an open-reading frame of 1089 bp (identified based on the G+C content relating to codon position). The alternative 'GTG' start codon was used, and this was preceded (8 bps upstream) by a Shine-Dalgarno motif. The gene mtb2-92 encoded a protein (termed MTB2-92) containing 363 amino acid residues with a predicted molecular weight of 40,436.4 Da.

Sequence homology comparisons of the predicted amino acid sequence of MTB2-92 with known proteins in the database indicated similarity to the cytochrome c oxidase subunit II of many different organisms. This integral membrane protein is part of the electron transport chain, subunits I and II forming the functional core of the enzyme complex.

1. Cloning the Full Length Gene Corresponding to HinP #2-92

The plasmid pHin2-92 was restricted with either BamH1 or EcoRI and then subcloned into the vector M13. The insert DNA fragments were sequenced under the direction of M13 universal sequencing primers (Yanisch-Perron, C. et al., 1985) using the AmpliCycle thermal sequencing kit (Perkin Elmer, Applied Biosystems Division, 850 Lincoln Centre Drive, Foster City, Calif. 94404, U.S.A.). The 5'-partial MTB2-92 DNA sequence was aligned using a GeneWorks (Intelligenetics, Mountain View, Calif., U.S.A.) program. Based on the sequence data obtained, two oligomers were synthesized. These oligonucleotides (5' CCCAGCTTGTGATACAGGAGG 3' (Seq. I.D. No. 106) and 5' GGCCTCAGCGCGGCTCCGGAGG 3' (Seq. I.D. No. 107)) represented sequences upstream and downstream, over an 0.8 kb distance, of the sequence encoding the partial MTB2-92 protein in the alkaline phosphatase fusion.

A *Mycobacterium tuberculosis* genomic cosmid DNA library was screened using PCR (Sambrook, J. et al., 1989) in order to obtain the full-length gene encoding the MTB2-92 protein. Two hundred and ninety-four bacterial colonies containing the cosmid library were pooled into 10 groups in 100 $\mu$l distilled water aliquots and boiled for 5 min. The samples were spun in a microfuge at maximal speed for 5 min. The supernatants were decanted and stored on ice prior to PCR analysis. The 100 $\mu$l-PCR reaction contained: 10 $\mu$l supernatant containing cosmid DNA, 10 $\mu$l of 10X PCR buffer, 250 $\mu$M dNTP's, 300 nM downstream and upstream primers, 1 unit Taq DNA polymerase.

The reactions were heated at 95° C. for 2 min and then 40 cycles of DNA synthesis were performed (95° C. for 30 s, 65° C. for 1 min, 72° C. for 2 min). The PCR products were loaded into a 1% agarose gel in TAE buffer (Sambrook, J. et al., 1989) for analysis.

The supernatant, which produced 800 bp PCR products, was then further divided into 10 samples and the PCR reactions were performed again. The colony which had resulted in the correctly sized PCR product was then picked. The cosmid DNA from the positive clone (pG3) was prepared using the Wizard Mini-Prep Kit (Promega Corp, Madison, Wis., U.S.A.). The cosmid DNA was further sequenced using specific oligonucleotide primers. The deduced amino acid sequence encoded by the MTB2-92 protein is shown in FIG. 1.

2. Expression of the Full Length Gene

To conveniently purify the recombinant protein, a histidine tag coding sequence was engineered immediately upstream of the start codon of mtb2-92 using PCR. Two unique restriction enzyme sites for XbaI and HindIII were added to both ends of the PCR product for convenient subcloning. Two oligomers were used to direct the PCR reaction: (5' TCTAGACACCACCACCACCACCACGT- GACAC CTCGCGGGCCAGGTC 3' (Seq. I.D. No. 108) and 5' AAGCTTCGCCATGCCGC CGGTAAGCGCC 3' (Seq. I.D. No. 109)).

The 100 $\mu l$ PCR reaction contained: 1 $\mu g$ pG3 template DNA, 250 $\mu M$ dNTP's, 300 nM of each primer, 10 $\mu l$ of 10X PCR buffer, 1 unit Taq DNA polymerase. The PCR DNA synthesis cycle was performed as above.

The 1.4 kb PCR products were purified and ligated into the cloning vector pGEM-T (Promega). Inserts were removed by digestion using both the XbaI and HindIII and the 1.4 kb fragment was directionally subcloned into the XbaI and HindIII sites of pMAL-c2 vector (New England Bio-Labs Ltd., 3397 American Drive, Unit 12, Mississauga, Ontario, L4V 1T8, Canada). The gene encoding MTB2-92 was fused, in frame, downstream of the maltose binding protein (MBP). This expression vector was named pMAL-MTB2-92.

3. Purification of the Encoded Protein

The plasmid pMAL-MTB2-92 was transformed into competent *E. coli* JM109 cells and a 1 liter culture was grown up in LB broth at 37° C. to an $OD_{550}$ of 0.5 to 0.6. The expression of the gene was induced by the addition of IPTG (0.5 mM) to the culture medium, after which the culture was grown for another 3 hours at 37° C. with vigorous shaking. Cultures were spun in the centrifuge at 10,000 g for 30 min and the cell pellet was harvested. This was re-suspended in 50 ml of 20 mM Tris-HCl, pH 7.2, 200 mM NaCl, 1 mM EDTA supplemented with 10 mM β mercaptoethanol and stored at −20° C.

The frozen bacterial suspension was thawed in cold water (0° C.), placed in an ice bath, and sonicated. The resulting cell lysate was then centrifuged at 10,000 g and 4° C. for 30 min, the supernatant retained, diluted with 5 volumes of buffer A and applied to an amylose-resin column (New England Bio-Labs Ltd., 3397 American Drive, Unit 12, Mississauga, Ontario, L4V 1T8, Canada) which had been pre-equilibrated with buffer A. The column was then washed with buffer A until the eluate reached an $A_{280}$ of 0.001 at which point, the bound MBP-MTB2-92 fusion protein was eluted with buffer A containing 10 mM maltose. The protein purified by the amylose-resin affinity column was about 84 kDa which corresponded to the expected size of the fusion protein (MBP: 42 kDa, MTB2-92 plus the histidine tag: 42 kDa).

The eluted MBP-MTB2-92 fusion protein was then cleaved with factor Xa to remove the MBP from the MTB2-92 protein. One ml of fusion protein (1 mg/ml) was mixed with 100 $\mu l$ of factor Xa (200 $\mu g$/ml) and kept at room temperature overnight. The mixture was diluted with 10 ml of buffer B (5 mM imidazole, 0.5 M NaCl, 20 mM Tris-HCl, pH 7.9, 6 M urea) and urea was added to the sample to a final concentration of 6 M urea. The sample was loaded onto the Ni-NTA column (QIAGEN, 9600 De Soto Ave., Chatsworth, Calif. 91311, U.S.A.) pre-equilibrated with buffer B. The column was washed with 10 volumes of buffer B and 6 volumes of buffer C (60 mM imidazole, 0.5 M NaCl, 20 mM Tris-HCl, pH 7.9, 6 M urea). The bound protein was eluted with 6 volumes of buffer D (1 M imidazole, 0.5 M NaCl, 20 mM Tris-HCl, pH 7.9, 6 M urea).

At each stage of the protein purification, a sample was analysed by SDS polyacylamide gel electrophoresis (Laemmli, U.S. (1970) *Nature* (*London*), 227:680–685).

C. Correction of Sequence Errors

It is noted that some of the sequences presented in the Sequence Listing contain sequence ambiguities. Naturally, in order to ensure that the immunostimulatory function is maintained, one would utilize a sequence without such ambiguities. For those sequences containing ambiguities, one would therefore utilize the sequence data provided in the Sequence Listing to design primers corresponding to each terminal of the provided sequence and, using these primers in conjunction with the polymerase chain reaction, synthesize the desired DNA molecule using *M. tuberculosis* genomic DNA as a template. Standard PCR methodologies, such as those described above, may be used to accomplish this.

VI. EXPRESSION AND PURIFICATION OF THE CLONED PEPTIDES

Having provided herein DNA sequences encoding *Mycobacterium tuberculosis* peptides having an immunostimulatory activity, as well as the corresponding full length *Mycobacterium tuberculosis* genes, one of skill in the art will be able to express and purify the peptides encoded by these sequences. Methods for expressing proteins by recombinant means in compatible prokaryotic or eukaryotic host cells are well known in the art and are discussed, for example, in reference nos. 15 and 16. Peptides expressed by the nucleotide sequences disclosed herein are useful for preparing vaccines effective against *M. tuberculosis* infection, for use in diagnostic assays and for raising antibodies that specifically recognize *M. tuberculosis* proteins. One method of purifying the peptides is that presented in part V(B) above.

The most commonly used prokaryotic host cells for expressing prokaryotic peptides are strains of *Escherichia coli,* although other prokaryotes, such as *Bacillus subtilis* Streptomyces or Pseudomonas may also be used, as is well known in the art. Partial or full-length DNA sequences, encoding an immunostimulatory peptide according to the present invention, may be ligated into bacterial expression vectors. One aspect of the present invention is thus a recombinant DNA vector including a nucleic acid molecule provided by the present invention. Another aspect is a transformed cell containing such a vector.

Methods for expressing large amounts of protein from a cloned gene introduced into *Escherichia coli* (*E. coli*) may be utilized for the purification of the *Mycobacterium tuberculosis* peptides. Methods and plasmid vectors for producing fusion proteins and intact native proteins in bacteria are described in reference no. 15 (ch. 17). Such fusion proteins may be made in large amounts, are relatively simple to purify, and can be used to produce antibodies. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy.

Often, proteins expressed at high levels are found in insoluble inclusion bodies. Methods for extracting proteins from these aggregates are described in ch. 17 of reference no. 15. Vector systems suitable for the expression of lacZ fusion genes include the pUR series of vectors (24), pEX1-3 (25) and pMR100 (26). Vectors suitable for the production of intact native proteins include pKC30 (27), pKK177-3 (28) and pET-3 (29). Fusion proteins may be isolated from protein gels, lyophilized, ground into a powder and used as antigen preparations.

Mammalian or other eukaryotic host cells, such as those of yeast, filamentous fungi, plant, insect, amphibian or avian species, may also be used for protein expression, as is well known in the art. Examples of commonly used mammalian host cell lines are VERO and HeLa cells, Chinese hamster ovary (CHO) cells, and WI38, BHK, and COS cell lines, although it will be appreciated by the skilled practitioner that other prokaryotic and eukaryotic cells and cell lines may be appropriate for a variety of purposes, e.g., to provide higher expression, desirable glycosylation patterns, or other features.

Additionally, peptides, particularly shorter peptides, may be chemically synthesized, avoiding the need for purification from cells or culture media. It is known that peptides as short as 5 amino acids can act as an antigenic determinant and stimulate an immune response. Such peptides may be administered as vaccines in ISCOMs (Immune Stimulatory Complexes) as described by Janeway & Travers, Immunobiology: The Immune System In Health and Disease, 13.21 (Garland Publishing, Inc. New York, 1997). Accordingly, one aspect of the present invention includes small peptides encoded by the nucleic acid molecules disclosed herein. Such peptides include at least 5, and preferably 10 or more, contiguous amino acids of the peptides encoded by the disclosed nucleic acid molecules.

VII. SEQUENCE VARIANTS

It will be apparent to one skilled in the art that the immunostimulatory activity of the peptides encoded by the DNA sequences disclosed herein lies not in the precise nucleotide sequence of the DNA sequences, but rather in the epitopes inherent in the amino acid sequences encoded by the DNA sequences. It will therefore also be apparent that it is possible to recreate the immunostimulatory activity of one of these peptides by recreating the epitope, without necessarily recreating the exact DNA sequence. This could be achieved either by directly synthesizing the peptide (thereby circumventing the need to use the DNA sequences) or, alternatively, by designing a nucleic acid sequence that encodes for the epitope, but which differs, by reason of the redundancy of the genetic code, from the sequences disclosed herein.

Accordingly, the degeneracy of the genetic code further widens the scope of the present invention as it enables major variations in the nucleotide sequence of a DNA molecule while maintaining the amino acid sequence of the encoded protein. The genetic code and variations in nucleotide codons for particular amino acids is presented in Tables 5 and 6. Based upon the degeneracy of the genetic code, variant DNA molecules may be derived from the DNA sequences disclosed herein using standard DNA mutagenesis techniques, or by synthesis of DNA sequences.

TABLE 5

The Genetic Code

| First | Second Pos'n | | | | Third |
|---|---|---|---|---|---|
| Pos'n | T | C | A | G | Pos'n |
| T | Phe | Ser | Tyr | Cys | T |
| | Phe | Ser | Tyr | Cys | C |
| | Leu | Ser | Stop (och) | Stop | A |
| | Leu | Ser | Stop (amb) | Trp | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |

TABLE 5-continued

The Genetic Code

| First | Second Pos'n | | | | Third |
|---|---|---|---|---|---|
| Pos'n | T | C | A | G | Pos'n |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Val (Met) | Ala | Glu | Gly | G |

"Stop (och)" stands for the ocre termination triplet, and "Stop (amb)" for the amber. ATG is the most common initiator codon; GTG usually codes for valine, but it can also code for methionine to initiate an mRNA chain.

TABLE 6

The Degeneracy of the Genetic Code

| Number of Synontmous Codons | Amino Acid | Total Number of Codons |
|---|---|---|
| 6 | Leu, Ser, Arg | 18 |
| 4 | Gly, Pro, Ala, Val, Thr | 20 |
| 3 | Ile | 3 |
| 2 | Phe, Tyr, Cys, His, Gln, Glu, Asn, Asp, Lys | 18 |
| 1 | Met, Trp | 2 |
| Total number of codons for amino acids | | 61 |
| Number of codons for termination | | 3 |
| Total number of codons in genetic code | | 64 |

Additionally, standard mutagenesis techniques may be used to produce peptides which vary in amino acid sequence from the peptides encoded by the DNA molecules disclosed herein. However, such peptides will retain the essential characteristic of the peptides encoded by the DNA molecules disclosed herein, i.e. the ability to stimulate INF-γ production. This characteristic can readily be determined by the assay technique described above. Such variant peptides include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

In order to maintain the functional epitope, preferred peptide variants will differ by only a small number of amino acids from the peptides encoded by the DNA sequences disclosed herein. Preferably, such variants will be amino acid substitutions of single residues. Substitutional variants are those in which at least one residue in the amino acid sequence has been removed and a different residue inserted in its place. Such substitutions generally are made in accordance with the following Table 7 when it is desired to finely modulate the characteristics of the protein. Table 7 shows amino acids which may be substituted for an original amino acid in a protein and which are regarded as conservative substitutions. As noted, all such peptide variants are tested to confirm that they retain the ability to stimulate INF-γ production.

TABLE 7

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in immunological identity are made by selecting substitutions that are less conservative than those in Table 7, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. However, such variants must retain the ability to stimulate INF-γ production.

VIII. USE OF CLONED MYCOBACTERIUM SEQUENCES TO PRODUCE VACCINES

The purified peptides encoded by the nucleotide sequences of the present invention may be used directly as immunogens for vaccination. The conventional tuberculosis vaccine is the BCG (bacille Calmette-Guerin) vaccine, which is a live vaccine comprising attenuated *Mycobacterium bovis* bacteria. However, the use of this vaccine in a number of countries, including the U.S., has been limited because administration of the vaccine interferes with the use of the tuberculin skin test to detect infected individuals (see *Cecil Textbook of Medicine* (Ref. 33), pages 1733–1742 and section VIII (2) below).

The present invention provides a possible solution to the problems inherent in the use of the BCG vaccine in conjunction with the tuberculin skin test. The solution proposed is based upon the use of one or more of the immunostimulatory *M. tuberculosis* peptides disclosed herein as a vaccine and one or more different immunostimulatory *M. tuberculosis* peptides disclosed herein in the tuberculosis skin test (see section IX (2) below). If the immune system is primed with such a vaccine, it will be able to resist an infection by *M. tuberculosis*. However, exposure to the vaccine peptides alone will not induce an immune response to those peptides that are reserved for use in the tuberculin skin test. Thus, the present invention would allow the clinician to distinguish between a vaccinated individual and an infected individual.

Methods for using purified peptides as vaccines are well known in the art and are described in the following publications: Pal and Horwitz (1992) (reference no. 8) (describing immunization with extra-cellular proteins of *Mycobacterium tuberculosis*); Yang et al. (1991) (reference no. 30) (vaccination with synthetic peptides corresponding to the amino acid sequence of a surface glycoprotein from *Leishmania major*); Andersen (1994) (reference no. 9) (vaccination using short-term culture filtrate containing proteins secreted by *Mycobacterium tuberculosis*); and Jardim et al. (1990) (reference no. 10) (vaccination with synthetic T-cell epitopes derived from Leishmania parasite). Methods for preparing vaccines which contain immunogenic peptide sequences are also disclosed in U.S. Pat. Nos. 4,608,251, 4,601,903, 4,599,231, 4,5995230, 4,596,792 and 4,578,770. The formulation of peptide-based vaccines employing *M. tuberculosis* peptides is also discussed extensively in International Patent application WO 95/01441.

As is well known in the art, adjuvants such as Complete Freund's Adjuvant (CFA) and Incomplete Freund's Adjuvant (IFA) may be used in formulations of purified peptides as vaccines. Accordingly, one embodiment of the present invention is a vaccine comprising one or more immunostimulatory *M. tuberculosis* peptides encoded by genes including a sequence shown in the attached sequence listing, together with a pharmaceutically acceptable adjuvant.

Additionally, the vaccines may be formulated using a peptide according to the present invention together with a pharmaceutically acceptable excipient such as water, saline, dextrose and glycerol. The vaccines may also include auxiliary substances such as emulsifying agents and pH buffers.

It will be appreciated by one of skill in the art that vaccines formulated as described above may be administered in a number of ways including subcutaneous, intramuscular and intra-venous injection. Doses of the vaccine administered will vary depending on the antigenicity of the particular peptide or peptide combination employed in the vaccine, and characteristics of the animal or human patient to be vaccinated. While the determination of individual doses will be within the skill of the administering physician, it is anticipated that doses of between 1 microgram and 1 milligram will be employed.

As with many vaccines, the vaccines of the present invention may routinely be administered several times over the course of a number of weeks to ensure that an effective immune response is triggered. As described in International Patent Application WO 95/01441, up to six doses of the vaccine may be administered over a course of several weeks, but more typically between one and four doses are administered. Where such multiple doses are administered, they will normally be administered at from two to twelve week intervals, more usually from three to five week intervals. Periodic boosters at intervals of 1–5 years, usually three years, will be desirable to maintain the desired levels of protective immunity.

As described in WO 95/01441, the course of the immunization may be followed by in vitro proliferation assays of PBL (peripheral blood lymphocytes) co-cultured with ESAT6 or ST-CF, and especially by measuring the levels of IFN-γ released from the primed lymphocytes. The assays are well known and are widely described in the literature, including in U.S. Pat. Nos. 3,791,932; 4,174,384 and 3,949,064.

To ensure an effective immune response against tuberculosis infection, vaccines according to the present invention may be formulated with more than one immunostimulatory peptide encoded by the nucleotide sequences disclosed herein. In such cases, the amount of each purified peptide incorporated into the vaccine will be adjusted accordingly.

Alternatively, multiple immunostimulatory peptides may also be administered by expressing the nucleic acids encoding the peptides in a nonpathogenic microorganism, and using this transformed nonpathogenic microorganism as a vaccine. As described in International Patent Application WO 95/01441, *Mycobacterium bovis* BCG may be employed for this purpose, although this approach would destroy the advantage outlined above to be gained from using separate classes of the peptides as vaccines and in the skin test. As disclosed in WO 95/01441, an immunostimulatory peptide of *M. tuberculosis* can be expressed in the BCG bacterium by transforming the BCG bacterium with a nucleotide sequence encoding the *M. tuberculosis* peptide. Thereafter, the BCG bacteria can be administered in the same manner as a conventional BCG vaccine. In particular embodiments, multiple copies of the *M. tuberculosis* sequence are transformed into the BCG bacteria to enhance the amount of *M. tuberculosis* peptide produced in the vaccine strain.

Finally, a recent development in the field of vaccines is the direct injection of nucleic acid molecules encoding peptide antigens, as described in Janeway & Travers, Immunobiology: The Immune System In Health and Disease, 13.25 (Garland Publishing, Inc. New York, 1997); McDonnell & Askari, *N. Engl. J. Med.* 334:42–45 (1996). Thus, plasmids which include nucleic acid molecules described herein, or which include nucleic acid sequences encoding peptides according to the present invention may be utilized in such DNA vaccination methods.

IX. USE OF CLONED MYCOBACTERIUM SEQUENCES IN DIAGNOSTIC ASSAYS

Another aspect of the present invention is a composition for diagnosing tuberculosis infection wherein the composition includes peptides encoded by the nucleotide sequences of the present invention. The invention also encompasses methods and compositions for detecting the presence of anti-tuberculosis antibodies, tuberculosis peptides and tuberculosis nucleic acid sequences in body samples. Three examples typify the various techniques that may be used to diagnose tuberculosis infection using the present invention: an in vitro ELISA assay, an in vivo skin test assay and a nucleic acid amplification assay.

A. In Vitro ELISA Assay

One aspect of the invention is an ELISA that detects anti-tuberculosis mycobacterial antibodies in a medical specimen. An immunostimulatory peptide encoded by a nucleotide sequence of the present invention is employed as an antigen and is preferably bound to a solid matrix such as a crosslinked dextran such as SEPHADEX (Pharmacia, Piscataway, N.J.), agarose, polystyrene, or the wells of a microtiter plate. The polypeptide is admixed with the specimen, such as human sputum, and the admixture is incubated for a sufficient time to allow antimycobacterial antibodies present in the sample to immunoreact with the polypeptide. The presence of the immunopositive immunoreaction is then determined using an ELISA assay.

In a preferred embodiment, the solid support to which the polypeptide is attached is the wall of a microtiter assay plate. After attachment of the polypeptide, any nonspecific binding sites on the microtiter well walls are blocked with a protein such as bovine serum albumin. Excess bovine serum albumin is removed by rinsing and the medical specimen is admixed with the polypeptide in the microtiter wells. After a sufficient incubation time, the microtiter wells are rinsed to remove excess sample and then a solution of a second antibody, capable of detecting human antibodies is added to the wells. This second antibody is typically linked to an enzyme such as peroxidase, alkaline phosphatase or glucose oxidase. For example, the second antibody may be a peroxidase-labeled goat anti-human antibody. After further incubation, excess amounts of the second antibody are removed by rinsing and a solution containing a substrate for the enzyme label (such as hydrogen peroxide for the peroxidase enzyme) and a color-forming dye precursor, such as o-phenylenediamine is added. The combination of mycobacterium peptide (bound to the wall of the well), the human antimycobacterial antibodies (from the specimen), the enzyme-conjugated anti-human antibody and the color substrate will produce a color than can be read using an instrument that determines optical density, such as a spectrophotometer. These readings can be compared to a control incubated with water in place of the human body sample, or, preferably, a human body sample known to be free of antimycobacterial antibodies. Positive readings indicate the presence of anti-mycobacterial antibodies in the specimen, which in turn indicate a prior exposure of the patient to tuberculosis.

B. Skin Test Assay

Alternatively, the presence of tuberculosis antibodies in a patient's body may be detected using an improved form of the tuberculin skin test, employing immunostimulatory peptides of the present invention. Conventionally, this test produces a positive result to one of the following conditions: the current presence of *M. tuberculosis* in the patient's body; past exposure of the patient to *M. tuberculosis;* and prior BCG vaccination. As noted above, if one group of immunostimulatory peptides is reserved for use in vaccine preparations, and another group reserved for use in the improved skin test, then the skin test will not produce a positive response in individuals whose only exposure to tuberculosis antigens was via the vaccine. Accordingly, the improved skin test would be able to properly distinguish between infected individuals and vaccinated individuals.

The tuberculin skin test consists of an injection of proteins from *M. tuberculosis* that are injected intradermally. The test is described in detail in *Cecil Textbook of Medicine* (Ref. 33), pages 1733–1742. If the subject has reactive T-cells to the injected protein, the cells will migrate to the site of injection and cause a local inflammation. This inflammation, which is generally known as delayed type hypersensitivity (DTH) is indicative of *M. tuberculosis* antibodies in the patient's blood stream. Purified immunostimulatory peptides according to the present invention may be employed in the tuberculin skin test using the methods described in reference 33.

C. Nucleic Acid Amplification

One aspect of the invention includes nucleic acid primers and probes derived from the sequences set forth in the attached sequence listing, as well as primers and probes derived from the full length genes that can be obtained using these sequences. These primers and probes can be used to detect the presence of *M. tuberculosis* nucleic acids in body samples and thus to diagnose infection. Methods for making primers and probes based on these sequences are well known and are described in section V above.

The detection of specific pathogen nucleic acid sequences in human body samples by polymerase chain reaction amplification (PCR) is discussed in detail in reference 17, in particular, part four of that reference. To detect *M. tuberculosis* sequences, primers based on the sequences disclosed herein would be synthesized, such that PCR amplification of a sample containing *M. tuberculosis* DNA would result in an amplified fragment of a predicted size. If necessary, the presence of this fragment following amplification of the sample nucleic acid could be detected by dot blot analysis (see chapter 48 of reference 17). PCR amplification employing primers based on the sequences disclosed herein may also be employed to quantify the amounts of *M. tuberculosis* nucleic acid present in a particular sample (see chapters 8 and 9 of reference 17). Reverse-transcription PCR using these primers may also be utilized to detect the presence of *M. tuberculosis* RNA, indicative of an active infection.

Alternatively, probes based on the nucleic acid sequences described herein may be labelled with suitable labels (such a $P^{32}$ or biotin) and used in hybridization assays to detect the presence of *M. tuberculosis* nucleic acid in provided samples.

X. USE OF CLONED MYCOBACTERIUM SEQUENCES TO RAISE ANTIBODIES

Monoclonal antibodies may be produced to the purified *M. tuberculosis* peptides for diagnostic purposes. Substantially pure *M. tuberculosis* peptide suitable for use as an immunogen is isolated from the transfected or transformed cells as described above. The concentration of protein in the final preparation is adjusted, for example, by concentration on an Amicon filter device, to the level of a few milligrams per milliliter. Monoclonal antibody to the protein can then be prepared as follows:

A. Monoclonal Antibody Production by Hybridoma Fusion

Monoclonal antibody to epitopes of the *M. tuberculosis* peptides identified and isolated as described can be prepared from murine hybridomas according to the classical method of Kohler and Milstein (1975) or derivative methods thereof. Briefly, a mouse is repetitively inoculated with a few micrograms of the selected purified protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (1980), and derivative methods thereof. Selected positive clones can be expanded and their monoclonal antibody product harvested for use. Detailed procedures for monoclonal antibody production are described in Harlow and Lane (1988).

B. Antibodies Raised Against Synthetic Peptides

An alternative approach to raising antibodies against the *M. tuberculosis* peptides is to use synthetic peptides synthesized on a commercially available peptide synthesizer based upon the amino acid sequence of the peptides predicted from nucleotide sequence data.

In a preferred embodiment of the present invention, monoclonal antibodies that recognize a specific *M. tuberculosis* peptide are produced. Optimally, monoclonal antibodies will be specific to each peptide, i.e. such antibodies recognize and bind one *M. tuberculosis* peptide and do not substantially recognize or bind to other proteins, including those found in healthy human cells.

The determination that an antibody specifically detects a particular *M. tuberculosis* peptide is made by any one of a number of standard immunoassay methods; for instance, the Western blotting technique (Sambrook et al., 1989). To determine that a given antibody preparation (such as one produced in a mouse) specifically detects one *M. tuberculosis* peptide by Western blotting, total cellular protein is extracted from a sample of human sputum from a healthy patient and from sputum from a patient suffering from tuberculosis. As a positive control, total cellular protein is also extracted from *M. tuberculosis* cells grown in vitro. These protein preparations are then electrophoresed on a sodium dodecyl sulfate-polyacrylamide gel. Thereafter, the proteins are transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect the *M. tuberculosis* protein will, by this technique, be shown to bind to the *M. tuberculosis*-extracted sample at a particular protein band (which will be localized at a given position on the gel determined by its molecular weight) and to the proteins extracted from the sputum from the tuberculosis patient. No significant binding will be detected to proteins from the healthy patient sputum. Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-tuberculosis protein binding. Preferably, no antibody would be found to bind to proteins extracted from healthy donor sputum.

Antibodies that specifically recognize a *M. tuberculosis* peptide encoded by the nucleotide sequences disclosed herein are useful in diagnosing the presence of tuberculosis antigens in patients.

All publications and published patent documents cited in this specification are incorporated herein by reference to the same extent as if each individual publication or patent application was specifically and individually indicated to be incorporated by reference.

XI. REFERENCES

1. Skamene, E. (1989). Genetic control of susceptibility to Mycobacterial infections. *Ref. Infect. Dis.* 11:S394–S399.

2. Kaufmann, S. H. E. (1991). Role of T-Cell Subsets in Bacterial Infections. *Current Opinion in Immunology* 3:465–470.

3. Orme, I. M., et al. (1992). T Lymphocytes Mediating Protection and Cellular Cytolysis During the Course of Mycobacterium-Tuberculosis Infection—Evidence for Different Kinetics and Recognition of a Wide Spectrum of Protein Antigens. *Journal of Immunology* 148:189–196.

4. Daugelat, S., et al. (1992). Secreted Antigens of *Mycobacterium tuberculosis:* characterization with T Lymphocytes from Patients and Contacts after Two-Dimensional Separation. *J. Infect. Dis.* 166:186–190.

5. Barnes et al. (1989). Characterization of T Cell Antigens Associated with the Cell Wall Protein-Peptidoglycan Complex of *Mycobacterium tuberculosis*. *J. Immunol.* 143:2656–2662.

6. Collins et al. (1988). Biological activity of protein antigens isolated from *Mycobacterium tuberculosis* culture filtrate. *Infect. Immun.* 56:1260–1266.

7. Lamb et al. (1989). Identification of Mycobacterial Antigens Recognized by T Lymphocytes, *Rev. Infect. Dis.* 11:S443–S447.

8. Pal, P. G., et al. (1992). Immunization with Extracellular Proteins of *Mycobacterium tuberculosis* Induces Cell-Mediated Immune Responses and Substantial Protective Immunity in a Guinea Pig Model of Pulmonary Tuberculosis. *Infect. Immun.* 60:4781–4792.

9. Andersen (1994). *Infection & Immunity* 62:2536.

10. Jardim et al. (1990). Immunoprotective *Leishmania major* Synthetic T Cell Epitopes. *J. Exp. Med.* 172:645–648.

11. Orme et al. (1993). Cytokine Secretion by CD4 T Lymphocytes Acquired in Response to *Mycobacterium tuberculosis* Infection. *J. Immunology* 151:518–525.

12. Boesen et al. (1995). Human T-Cell Responses to Secreted Antigen Fractions of *Mycobacterium tuberculosis. Infection and Immunity* 63:1491–1497.

13. Mougneau et al. (1995). Expression Cloning of a Protective Leishmania Antigen. *Science* 268:536–566.

14. Yang et al. (1990). Oral *Salmonella typhimurium* ($AroA^-$) Vaccine Expressing a Major Leishmanial Surface Protein (gp63) Preferentially Induces T Helper 1 Cells and Protective Immunity Against Leishmaniasis. *J. Immunology* 145:2281–2285.

15. Sambrook et al. (1989). *Molecular Cloning: A Laboratory Manual,* 2nd ed., vol. 1–3, ed. Cold Spring Harbor Laboratory Press: Cold Spring Harbor, N.Y.

16. Ausubel et al., (1987). *Current Protocols in Molecular Biology,* ed. Greene Publishing and Wiley-Interscience: New York (with periodic updates).

17. Innis et al., (1990). *PCR Protocols: A Guide to Methods and Applications,* Academic Press: San Diego.

18. Kanehisa (1984). *Nuc. Acids Res.* 12:203–213, 1984.

19. Wetmur et al. (1968). *J. Mol. Biol.* 31:349–370.

20. Beaucage et al. (1981) *Tetra. Letts.* 22:1859–1862.

21. Matteucci et al. (1981). *J. Am. Chem. Soc.* 103:3185.

22. Jacobs et al. (1991) *METHODS IN ENZYMOLOGY* 204:537–555.

23. Earp et al. (1990). *Nucleic Acids Research* 18:3721–3729.

24. Ruther et al. (1983). *EMBO J.* 2:1791.

25. Stanley and Luzio (1984). *EMBO J.* 3:1429.

26. Gray et al. (1982). *Proc. Natl. Acad. Sci. USA* 79:6598.

27. Shimatake and Rosenberg (1981). *Nature* 292:128.

28. Amann and Brosius (1985). *Gene* 40:183.

29. Studiar and Moffatt (1986). *J. Mol. Biol.* 189:113.

30. Yang et al. (1991). Identification and Characterization of Host-Protective T-Cell Epitopes of a Major Surface Glycoprotein (gp63) from *Leishmania major. Immunology* 72:3–9.

31. Mdluli et al. (1995). New vectors for the in vitro generation of alkaline phosphatase fusions to proteins encoded by G+C-rich DNA. *Gene* 155:133–134.

32. Lim et al. (1995). Identification of *Mycobacterium tuberculosis* DNA Sequences Encoding Exported Proteins by Using phoA Gene Fusions. *J. Bact.* 177:59–65).

33. *Cecil Textbook of Medicine,* (1992, 19th edition), Wyngaarden et al, eds. W. B. Saunders, Philadelphia, Pa.

34. Hubbard et al. (1992). Immunization of mice with mycobacterial culture filtrate culture proteins. *Clin. exp. Immunol.* 87: 94–98.

I claim:

1. An isolated nucleic acid molecule consisting of a nucleotide sequence selected from the group consisting of SEQ ID NOs: 2, 4, 11, 15, 23, 34, 41, 61, and 67.

2. A purified immunostimulatory peptide encoded by a nucleic acid molecule according to claim 1.

3. An antibody that specifically binds to a peptide according to claim 2.

4. A method of making an immunostimulatory preparation comprising:

providing at least one purified immunostimulatory peptide according to claim 2; and combining the peptide with a pharmaceutically acceptable excipient.

5. A purified immunostimulatory peptide comprising at least 5 contiguous amino acids encoded by a nucleic acid sequence selected from the group consisting of SEQ ID NOs: 2, 4, 11, 15, 23, 34, 41, 61, and 67.

6. An immunostimulatory preparation comprising at least one peptide according to claim 5 and a pharmaceutically acceptable excipient.

7. A peptide according to claim 5 wherein the peptide includes at least 10 contiguous amino acids encoded by a nucleic acid sequence selected from the group consisting of SEQ ID NOs: 2, 4, 11, 15, 23, 34, 41, 61, and 67.

8. An immunostimulatory preparation comprising at least one peptide according to claim 7 and a pharmaceutically acceptable excipient.

9. An isolated nucleic acid molecule consisting of a nucleotide sequence selected form the group consisting of:

(a) SEQ ID NOs: 2, 4, 11, 15, 23, 34, 41, 61 and 67;

(b) nucleotide sequences complementary to a sequence defined in (a);

(c) nucleic acid molecules of at least 15 nucleotides in length which have at least 75% sequence identity with molecules defined in (a) or (b), wherein the nucleic acid molecule encodes an immunostimulatory peptide; and (d) nucleic acid molecules comprising at least 15 consecutive nucleotides of a molecule defined in (a).

10. A recombinant vector including a nucleic acid molecule according to claim 9.

11. A nucleic acid probe comprising a nucleic acid molecule according to claim 9 conjugated with a detectable label.

12. A transformed cell containing a vector according to claim 10.

13. A method of detecting the presence of *Mycobacterium tuberculosis* DNA in a sample comprising contacting the sample with a nucleic acid probe according to claim 11 and detecting hybridization products that include the nucleic acid probe.

14. A method of isolating a *Mycobacterium tuberculosis* gene which gene encodes an immunostimulatory peptide, the method comprising the steps of:

providing nucleic acids of *Mycobacterium tuberculosis;* contacting said nucleic acids with a probe or primer, the probe or primer comprising at least 15 consecutive nucleotides of a sequence selected form the group consisting of SEQ ID NOs: 2, 4, 11, 15, 23, 34, 41, 61, and 67 and sequences complementary thereto;

identifying a gene hybridized to the probe or primer; and isolating the *Mycobacterium tuberculosis* gene, wherein the gene encodes an immunostimulatory peptide.

15. An isolated *Mycobacterium tuberculosis* nucleic acid molecule, said molecule encoding an immunostimulatory peptide and having at least 75% sequence identity with a nucleic acid probe comprising at least 15 contiguous bases of a sequence selected from SEQ ID NOs: 2, 4, 11, 15, 23, 34, 41, 61, and 67.

16. A purified immunostimulatory peptide encoded by the nucleic acid molecule of claim 15.

17. An immunostimulatory preparation comprising:

a purified peptide according to claim 16; and a pharmaceutically acceptable excipient.

18. An improved tuberculin skin test, the improvement comprising the use of one or more immunostimulatory peptides according to claim 16.

19. An immunostimulatory peptide encoded by a nucleic acid molecule selected from the group consisting of SEQ ID NOs: 2, 4, 11, 15, 23, 34, 41, 61, and 67, wherein the immunostimulatory peptide further comprises at least one conservative amino acid substitution.

20. An isolated *Mycobacterium tuberculosis* nucleic acid molecule consisting of a nucleotide sequence selected from the group consisting of SEQ ID NOs: 2, 4, 11, 15, 23, 34, 41, 61, and 67.

21. A vector comprising the isolated *Mycobacterium tuberculosis* nucleic acid molecule as recited in claim 20.

22. A purified immunostimulatory peptide comprising at least 5 contiguous amino acids encoded by a *Mycobacterium tuberculosis* nucleic acid sequence consisting of a nucleic acid sequence selected from the group consisting of SEQ ID NOs: 2, 4, 11, 15, 23, 34, 41, 61, and 67, wherein the nucleic acid molecule encodes a peptide that is expressed externally by *Mycobacterium tuberculosis.*

23. An isolated nucleic acid molecule consisting of a *Mycobacterium tuberculosis* nucleotide sequence selected from the group consisting of SEQ ID NOs: 2, 4, 11, 15, 23, 34, 41, 61, and 67, wherein the nucleic acid molecule encodes a peptide that is expressed externally by *Mycobacterium tuberculosis.*

* * * * *

UNITED STATES PATENT AND TRADEMARK OFFICE

CERTIFICATE OF CORRECTION

PATENT NO. : 6,228,371 B1
DATED : May 8, 2001
INVENTOR(S) : Dr. Francis E. Nano

It is certified that error appears in the above-identified patent and that said Letters Patent is hereby corrected as shown below:

Column 8,
Line 16, "nice" should be -- mice --.

Column 10,
Line 7, in Table 1, the column heading "INT" should be -- INF --.

Column 11,
Line 6, in Table 2, the column heading "INT" should be -- INF --.

Column 12,
Line 18, "fill" should be -- full --.

Column 13,
Line 64, the Peptide Sequence for Seq. I.D. No. 94, shown as "WIFQWNRLPRLVHLACI" should be -- WIFGWNRLPRLVHLACI --.

Column 28,
Line 31, "J. Bact. 177:59-65)." should be -- J. Bact. 177:59-65. --.

Signed and Sealed this

Twenty-first Day of May, 2002

*Attest:*

JAMES E. ROGAN

*Attesting Officer* *Director of the United States Patent and Trademark Office*